US012665089B2

(12) United States Patent
Yip et al.

(10) Patent No.: US 12,665,089 B2
(45) Date of Patent: Jun. 23, 2026

(54) MULTIMODAL SYSTEM AND METHOD FOR PREDICTING CANCER

(71) Applicant: Janssen Research & Development, LLC, Raritan, NJ (US)

(72) Inventors: Stephen S.F. Yip, Randolph, MA (US); Pooya Mobadersany, Coralville, IA (US); Jose Zamalloa, Lawrence Township, NJ (US); Justin Lucas, Bridgewater, NJ (US)

(73) Assignee: Janssen Research & Development, LLC, Raritan, NJ (US)

( * ) Notice: Subject to any disclaimer, the term of this patent is extended or adjusted under 35 U.S.C. 154(b) by 67 days.

(21) Appl. No.: 18/689,524

(22) PCT Filed: Sep. 8, 2022

(86) PCT No.: PCT/IB2022/058486
§ 371 (c)(1),
(2) Date: Mar. 6, 2024

(87) PCT Pub. No.: WO2023/037298
PCT Pub. Date: Mar. 16, 2023

(65) Prior Publication Data
US 2024/0379237 A1 Nov. 14, 2024

Related U.S. Application Data

(60) Provisional application No. 63/241,853, filed on Sep. 8, 2021.

(51) Int. Cl.
*G16H 50/20* (2018.01)
*G06N 3/0464* (2023.01)
*G16H 30/40* (2018.01)

(52) U.S. Cl.
CPC .......... *G16H 50/20* (2018.01); *G06N 3/0464* (2023.01); *G16H 30/40* (2018.01)

(58) Field of Classification Search
CPC ....... G16H 50/20; G16H 30/40; G06N 3/0464
See application file for complete search history.

(56) References Cited

U.S. PATENT DOCUMENTS

2016/0074570 A1 * 3/2016 Cho .................... A61M 1/3496
210/257.2
2016/0253466 A1 * 9/2016 Agaian .................. G06N 5/043
382/128

(Continued)

FOREIGN PATENT DOCUMENTS

CA 2948499 A1 * 5/2018 .............. G06T 7/11
CN 111275130 6/2020

(Continued)

OTHER PUBLICATIONS

Kumar et al., "An Ensemble of Fine-Tuned Convolutional Neural Networks for Medical Image Classification," IEEE Journal of Biomedical and Health Informatics, vol. 21, No. 1, Jan. 2017; Digital Object Identifier 10.1109/JBHI.2016.2635663. (Year: 2016).*

(Continued)

*Primary Examiner* — Jonathon A. Szumny
(74) *Attorney, Agent, or Firm* — Amsel IP Law PLLC; Jason Amsel

(57) ABSTRACT

Disclosed herein are methods for generating a cancer prediction for one or more patients, including obtaining or having obtained a first batch of images captured from the one or more patients; generating a first set of output values by providing, as input, the first batch of images to a first convolutional neural network, generating a second set of output values by providing, as input, interpretable features of the first batch of images to a first machine learning model; and generating a third set of output values informative of the (Continued)

cancer prediction by providing, as input, at least the first set of output values and the second set of output values to a fully connected network (FCN). The first convolutional neural network identifies one or more non-interpretable features from the first batch of images to generate the first set of output values.

20 Claims, 17 Drawing Sheets

(56) References Cited

U.S. PATENT DOCUMENTS

| | | | |
|---|---|---|---|
| 2017/0140114 A1 | 5/2017 | Are | |
| 2019/0164287 A1* | 5/2019 | Gregson | G16H 30/40 |
| 2020/0342955 A1 | 10/2020 | Guo | |
| 2020/0372638 A1* | 11/2020 | Gregson | G16H 50/70 |
| 2020/0372654 A1* | 11/2020 | Kohl | G06T 7/0012 |
| 2021/0090247 A1* | 3/2021 | Jeon | G06N 3/088 |
| 2021/0374954 A1* | 12/2021 | Yarlagadda | G06V 10/7784 |
| 2022/0167928 A1* | 6/2022 | Baek | A61B 5/7264 |
| 2022/0237777 A1* | 7/2022 | Kim | G16H 50/20 |
| 2022/0238208 A1* | 7/2022 | Sengupta | G16H 50/30 |
| 2022/0309295 A1* | 9/2022 | Wang | G06T 7/0012 |
| 2023/0030313 A1* | 2/2023 | Ahn | G16H 50/70 |
| 2023/0056839 A1* | 2/2023 | Ce-Ougna | G16H 30/40 |
| 2023/0089026 A1* | 3/2023 | Tran | A61B 6/48 |
| | | | 705/2 |
| 2023/0206441 A1* | 6/2023 | Zhong | G06V 20/49 |
| 2023/0207134 A1* | 6/2023 | Hegde | G06V 10/82 |
| | | | 382/133 |
| 2023/0237649 A1* | 7/2023 | Dillman | G16H 50/30 |
| | | | 382/128 |
| 2024/0013859 A1* | 1/2024 | Bai | G06N 20/20 |
| 2024/0127433 A1* | 4/2024 | Du | G16H 50/20 |

FOREIGN PATENT DOCUMENTS

| | | | | |
|---|---|---|---|---|
| CN | 112529892 A | * | 3/2021 | G06N 3/045 |
| WO | WO-2019191059 A1 | * | 10/2019 | G16H 10/60 |
| WO | WO-2020038771 A1 | * | 2/2020 | G06N 3/105 |
| WO | WO-2020149518 A1 | * | 7/2020 | G06T 7/0002 |
| WO | WO-2020190821 A1 | * | 9/2020 | G16H 10/20 |
| WO | 2021062366 | | 4/2021 | |

OTHER PUBLICATIONS

Wan et al., "Automated grading of breast cancer histopathology using cascaded ensemble with combination of multi-level image features," Neurocomputing 229 (2017) 34-44; http://dx.doi.org/10.1016/j.neucom.2016.05.084. (Year: 2017).*

Wang et al., "Cascaded Ensemble of Convolutional Neural Networks and Handcrafted Features for Mitosis Detection," Medical Imaging 2014: Digital Pathology, doi: 10.1117/12.2043902. (Year: 2014).*

Pereira et al., "Enhancing interpretability of automatically extracted machine learning features: application to a RBM-Random Forest system on brain lesion segmentation," Medical Image Analysis 44 (2018) 228-244; https://doi.org/10.1016/j.media.2017.12.009. (Year: 2018).*

Zhang et al., "MDNet: A Semantically and Visually Interpretable Medical Image Diagnosis Network," arXiv:1707.02485v1 [cs. CV] Jul. 8, 2017. (Year: 2017).*

Altaf Meteb M., "A hybrid deep learning model for breast cancer diagnosis based on transfer learning and pulse-coupled neural networks", Mathematical Biosciences and Engineering : MBE Oct. 2010, (Jan. 1, 2021), vol. 18, No. 5, doi: 10.3934/mbe.2021256, ISSN 1551-0018, pp. 5029-5046, XP093043871.

International Preliminary Report on Patentability issued in App. No. PCT/IB2022/058486, dated Mar. 5, 2024, 7 pages.

International Search Report and Written Opinion in PCT/IB2022/058486 mailed on Jan. 2, 2023, 12 pages.

International Search Report and Written Opinion issued in App. No. PCT/IB2022/058486, dated Jan. 2, 2023, 10 pages.

Yan Pingkun; Guo Hengtao; Wang Ge; Man Ruben De; Kalra Mannudeep K., "Hybrid Neural Networks for Mortality Prediction from LDCT Images", 2019 41st Annual International Conference of the IEEE Engineering in Medicine and Biology Society (EMBC), IEEE, (Jul. 23, 2019), doi: 10.1109/EMBC.2019.8857180, pp. 6243-6246, XP033625090.

Altaf Meteb M.: "A hybrid deep learning model for breast cancer diagnosis based on transfer learning and pulse-coupled neural networks", Mathematical Biosciences and Engineering : MBE Oct. 2010, vol. 18, No. 5, Jan. 1, 2021 (Jan. 1, 2021), pp. 5029-5046, XP093043871, ISSN: 1551-0018, DOI: 10.3934/mbe.2021256.

Amir Zadeh et al: "Tensor Fusion Network for Multimodal Sentiment Analysis", arxiv.org, Cornell University Library, 201 Olin Library Cornell University Ithaca, NY 14853, Jul. 23, 2017 (Jul. 23, 2017), XP080778826, 12 pages. DOI: 10.18653/V1/D17-1115.

Extended European Search Report issued in App. No. 22872307, dated May 16, 2025, 11 pages.

Yan Pingkun et al: "Hybrid Neural Networks for Mortality Prediction from LDCT Images", 2019 41st Annual International Conference of the IEEE Engineering in Medicine and Biology Society (EMBC), IEEE, Jul. 23, 2019 (Jul. 23, 2019), pp. 6243-6246, XP033625090, DOI: 10.1109/EMBC.2019.8857180 [retrieved on Oct. 2, 2019].

* cited by examiner

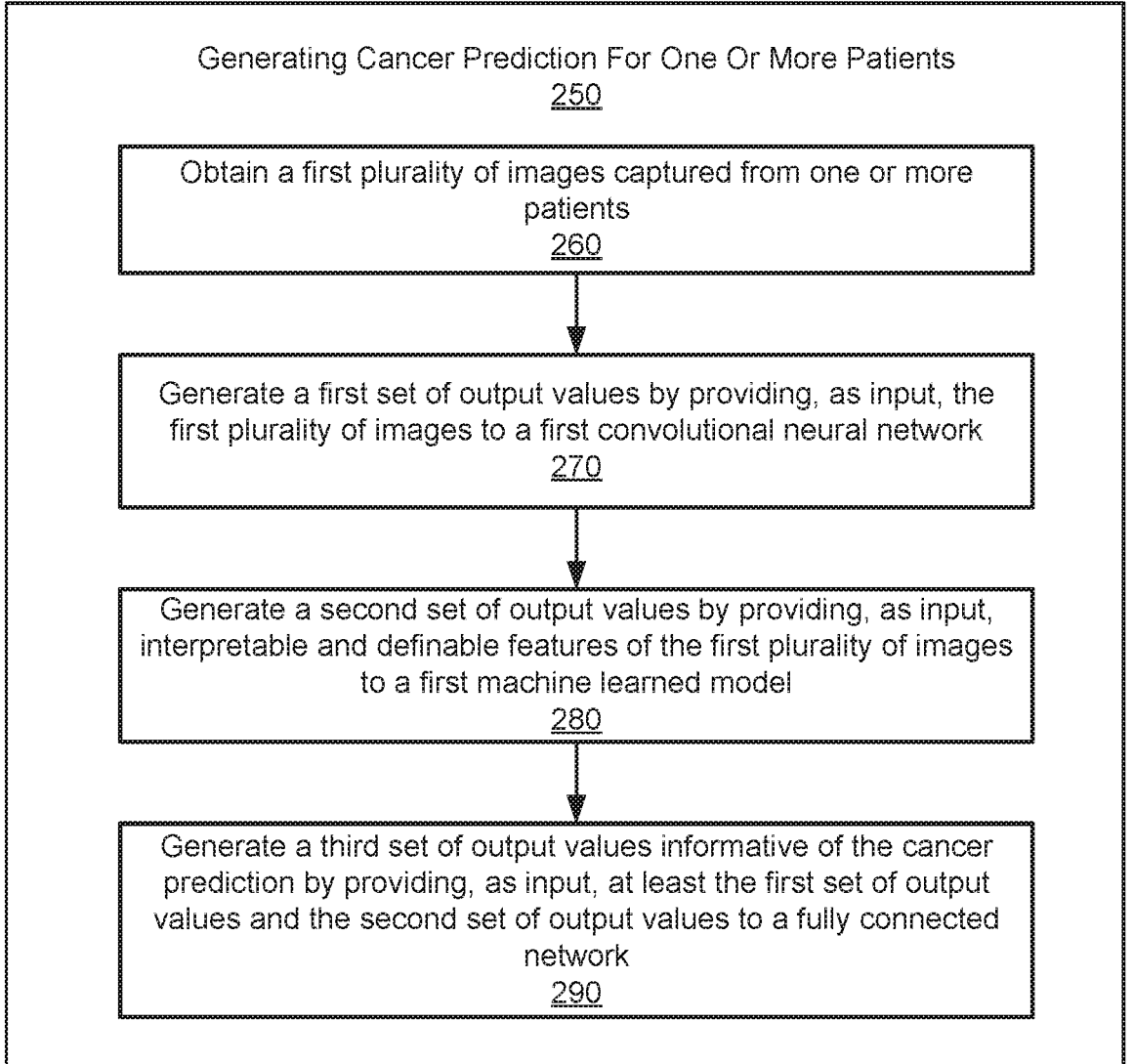

Generating Cancer Prediction For One Or More Patients
250

Obtain a first plurality of images captured from one or more patients
260

Generate a first set of output values by providing, as input, the first plurality of images to a first convolutional neural network
270

Generate a second set of output values by providing, as input, interpretable and definable features of the first plurality of images to a first machine learned model
280

Generate a third set of output values informative of the cancer prediction by providing, as input, at least the first set of output values and the second set of output values to a fully connected network
290

FIG. 2B

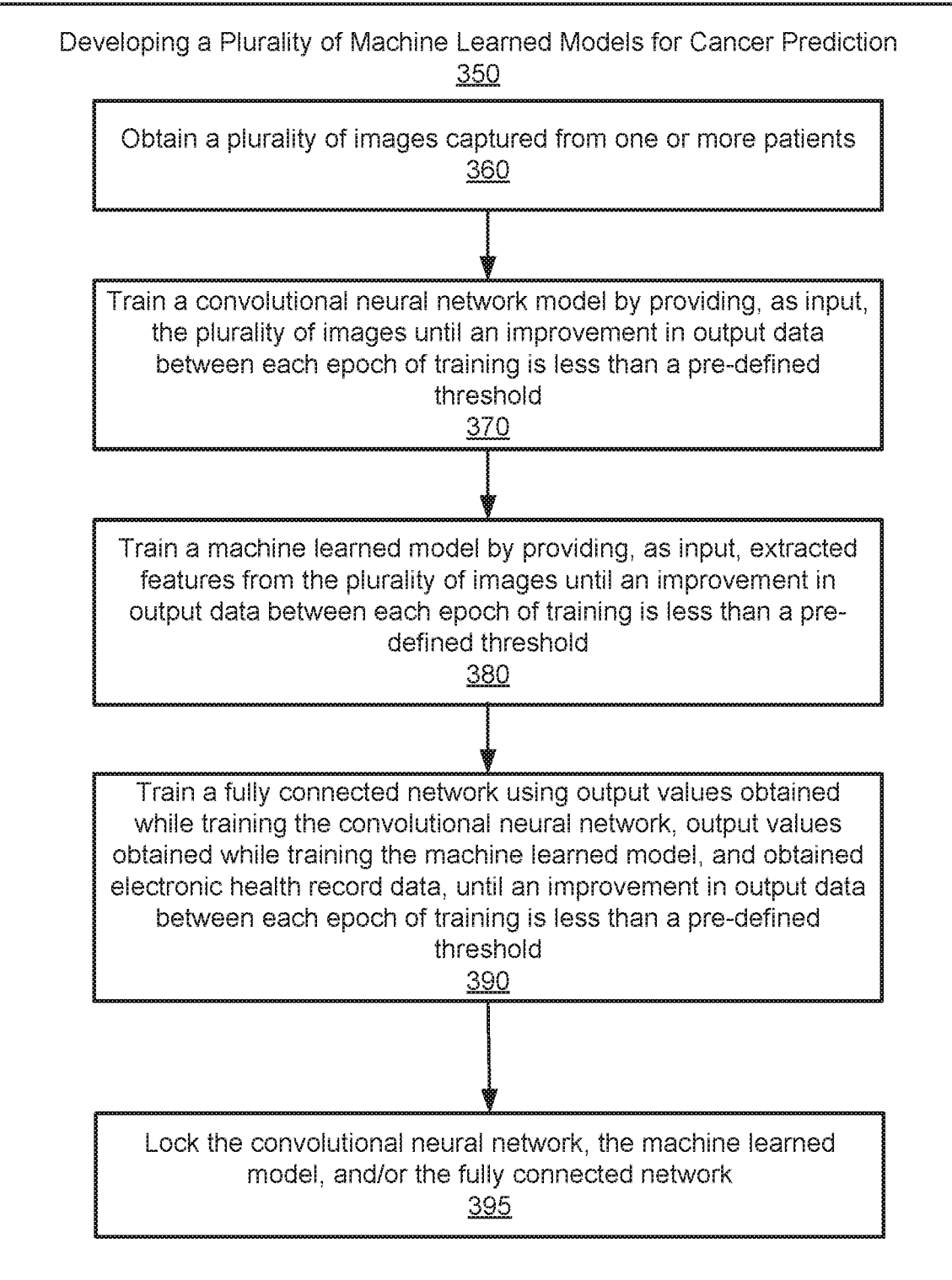

Developing a Plurality of Machine Learned Models for Cancer Prediction
350

Obtain a plurality of images captured from one or more patients
360

Train a convolutional neural network model by providing, as input, the plurality of images until an improvement in output data between each epoch of training is less than a pre-defined threshold
370

Train a machine learned model by providing, as input, extracted features from the plurality of images until an improvement in output data between each epoch of training is less than a pre-defined threshold
380

Train a fully connected network using output values obtained while training the convolutional neural network, output values obtained while training the machine learned model, and obtained electronic health record data, until an improvement in output data between each epoch of training is less than a pre-defined threshold
390

Lock the convolutional neural network, the machine learned model, and/or the fully connected network
395

FIG. 3B

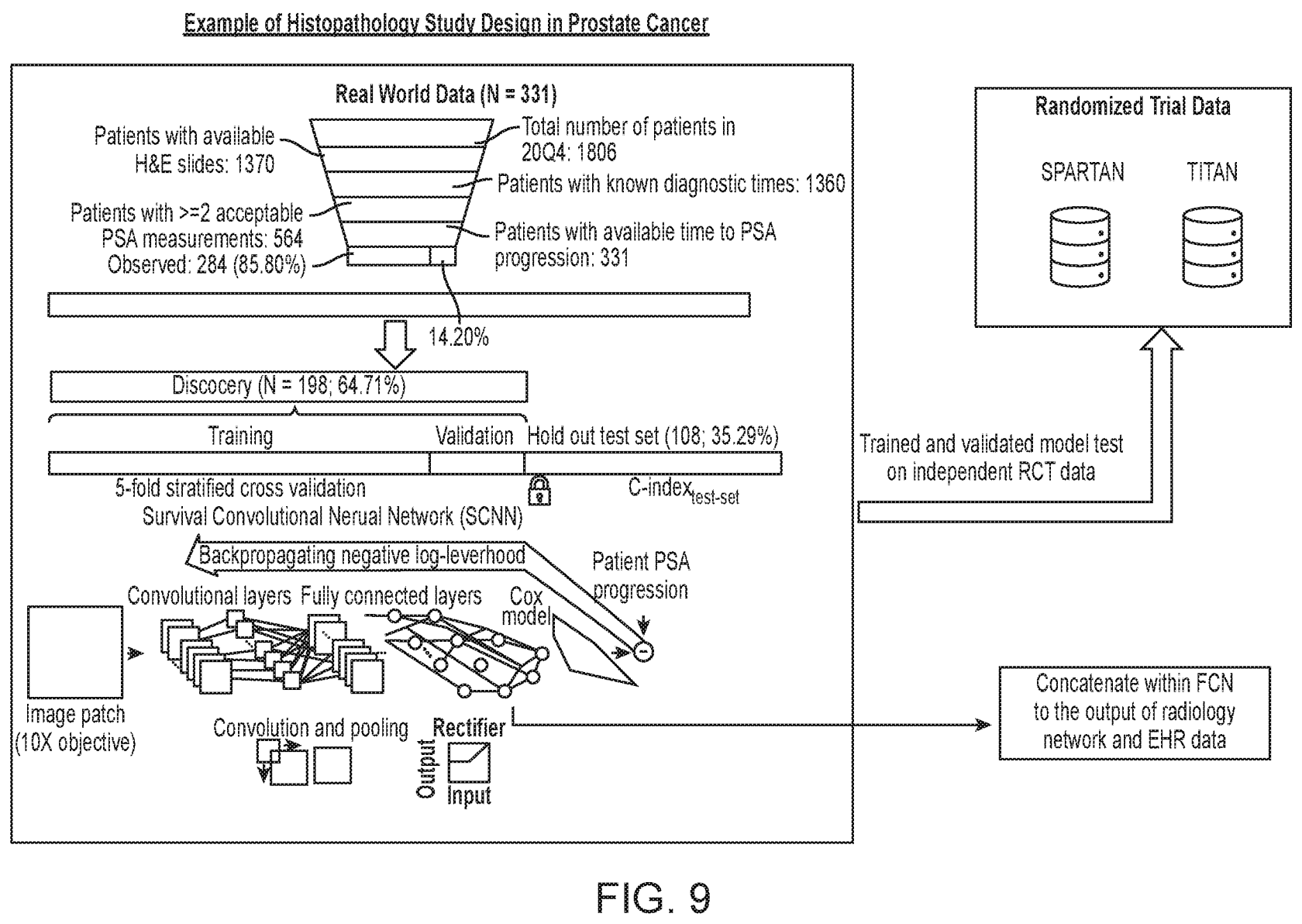

Example of Histopathology Study Design in Prostate Cancer

Real World Data (N = 331)

Patients with available H&E slides: 1370

Patients with >=2 acceptable PSA measurements: 564
Observed: 284 (85.80%)

Total number of patients in 20Q4: 1806

Patients with known diagnostic times: 1360

Patients with available time to PSA progression: 331

14.20%

Discocery (N = 198; 64.71%)

Training 5-fold stratified cross validation

Survival Convolutional Nerual Network (SCNN)

Validation    Hold out test set (108; 35.29%)

C-index_test-set

Backpropagating negative log-leverhood

Patient PSA progression

Convolutional layers  Fully connected layers

Cox model

Convolution and pooling   Rectifier

Output
Input

Image patch (10X objective)

Randomized Trial Data

SPARTAN        TITAN

Trained and validated model test on independent RCT data

Concatenate within FCN to the output of radiology network and EHR data

FIG. 9

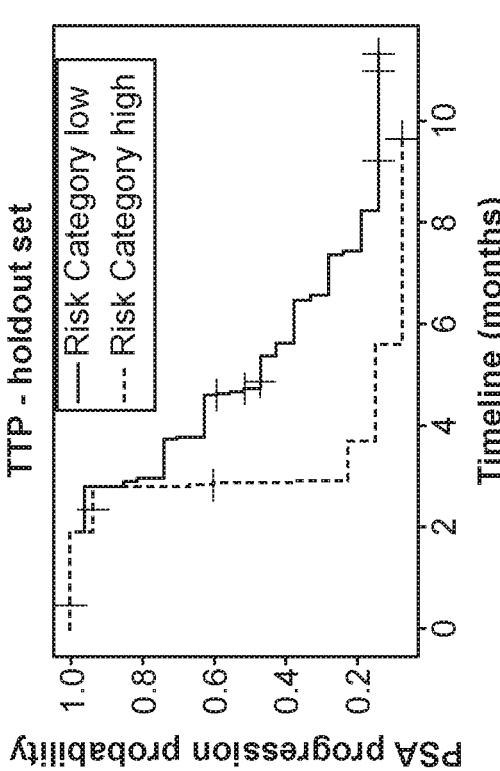
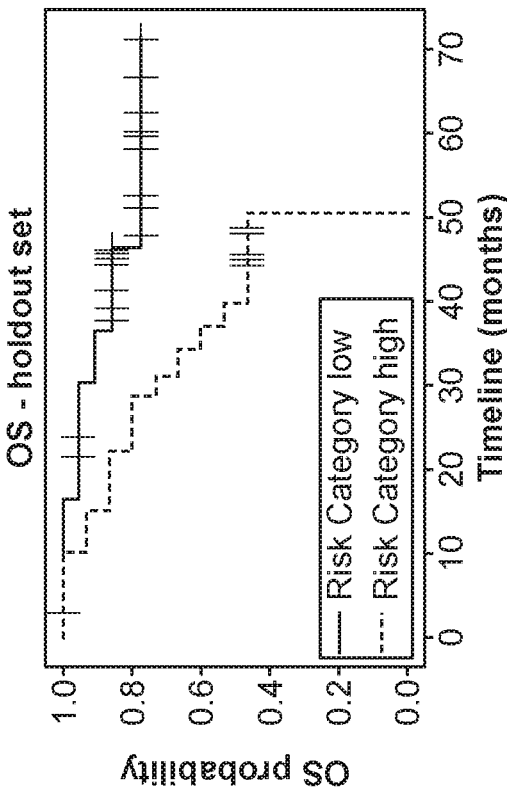
FIG. 11

| Endpoint | Overall survival (OS) | | | | | Time to PSA Progression (TTP) | | | | |
|---|---|---|---|---|---|---|---|---|---|---|
| Variable | H&E score | ECOGBL | PSABL | PSADT | Gleason | H&E score | ECOGBL | PSABL | PSADT | Gleason |
| HR | 2.59 | 0.79 | 1.01 | 0.70 | 1.12 | 1.11 | 1.72 | 1.01 | 0.5 | 1.05 |
| 95% CI | 2.14, 3.14 | 0.40, 1.58 | 0.99, 1.02 | 0.35, 1.41 | 0.88, 1.42 | 0.99, 1.24 | 1.09, 2.71 | 1.00, 1.02 | 0.32, 0.77 | 0.89, 1.24 |
| p | <0.005 | 0.50 | 0.20 | 0.32 | 0.34 | 0.07 | 0.02 | 0.01 | <0.005 | 0.58 |

ECOGBL: Baseline ECOG; PSABL: Baseline PSA; PSADT: PSA Doubling Time

FIG. 13

MULTIMODAL SYSTEM AND METHOD FOR PREDICTING CANCER

CROSS-REFERENCE TO RELATED APPLICATIONS

This application claims the benefit of U.S. Provisional Patent Application No. 63/241,853, which is incorporated by reference herein.

BACKGROUND

Despite advances in therapeutic options in cancer, the prognosis of cancers such as advanced non-small cell lung cancer (NSCLC) and prostate cancer, remains poor. A comprehensive multimodal framework that integrates different data types to achieve improved detection of cancer and evaluation of cancer progression is needed.

SUMMARY

Embodiments of the invention disclosed herein involve implementing a multimodal framework for early detection of cancer, predicting cancer therapeutic resistance, or predicting cancer progression patterns. The methods described herein are designed to solve data integration problems, and integrate both histopathology data (e.g., hematology-eosin (H&E) images), radiomic data (e.g., computed tomography (CT) or Positron emission tomography (PET)), and electronic health record (EHR) data to predict progression risk in cancer. The integration of radiomics, histopathology, and electronic health record (EHR) data into a framework enhances cancer predictions. The output predictions or identifications may enable (1) early treatment intensification, (2) novel treatment options, and (3) enrichment for high-risk population for clinical trial recruitment.

The multimodal framework can be useful for developing or supporting a clinician's treatment decision. For example, based on the models' predictions on the likelihood of prostate cancer progression under androgen-deprivation therapy (or therapeutic resistance), clinicians can decide whether or not to intensify treatment (e.g., use androgen receptor directed therapy) early. The multimodal framework can be useful for developing enhanced clinical trial recruitment, such as selecting high-risk patients for investigational therapy or treatment combination for clinical trials.

As described herein, systems, non-transitory computer readable media, and methods are used to integrate microscopic images (e.g., histopathology data) and macroscopic images (e.g., radiology data), which represent complementary natures of e.g., tumors, as well as electronic health record (EHR) data (e.g., demographic, smoking status, lab tests). The images and data are used to train and deploy a multimodal framework to determine, generate, or improve cancer predictions (e.g., progression or prognosis prediction in pan-cancer).

In a first embodiment, a method generates a cancer prediction for one or more patients. A first batch of images captured from the one or more patients is obtained. A first set of output values is generated by providing, as input, the first batch of images to a first convolutional neural network, wherein the first convolutional neural network identifies one or more non-interpretable features from the first batch of images to generate the first set of output values. A second set of output values is generated by providing, as input, interpretable and definable features of the first batch of images to a first machine learning model. A third set of output values is generated that is informative of the cancer prediction by providing, as input, at least the first set of output values and the second set of output values to a fully connected network (FCN).

In an embodiment, input values are further obtained for a batch of electronic health record data of the one or more patients. The first set and second set of output values and the input values of the batch of EHR data are concatenated. The third set of output values informative of the cancer prediction is generated in part by providing, as input, the EHR data to the neural network.

In an embodiment, the first batch of images captured from the one or more patients are processed. The interpretable and definable features are extracted from the first batch of images prior to generating a first set of output values.

In an embodiment, the first convolutional neural network model comprises any one of VGGNet, ResNet, and Inception.

In an embodiment, the first machine learning model comprises any one of logistic regression, cox proportional-hazards model, and random survival forest.

In an embodiment, a second batch of images captured from the one or more patients is obtained. A fourth set of output values is generated by providing, as input, the second batch of images to a second convolutional neural network, wherein the second convolutional neural network identifies one or more non-interpretable features from the second batch of images to generate the fourth set of output values. A fifth set of output values is generated by providing, as input, interpretable and definable features of the second batch of images to a second machine learning model. Generating the third set of output values informative of the cancer prediction further comprises providing, as input, the fourth set of output values and the fifth set of output values to the neural network.

In an embodiment, the second convolutional neural network model is any one of VGGNet, ResNet, and Inception.

In an embodiment, the second machine learning model is any one of logistic regression, cox proportional-hazards model, and random survival forest.

In an embodiment, the fully connected network comprises any one of a neural network, random forest, or support vector machine.

In an embodiment, the third set of output values informative of the cancer prediction comprises a composite risk index.

In an embodiment, the first batch of images comprise microscopic images or macroscopic images.

In an embodiment, the second batch of images comprise microscopic images or macroscopic images.

In an embodiment, the microscopic images comprise histology images, and wherein the histology images captures one or more cancer cells, lymphocytes, stromal cells, and epithelial cells.

In an embodiment, the macroscopic data comprises radiology images, and wherein the radiology images captures one or more tumor areas, surrounding areas in proximity to the tumor area, and lymph nodes.

In an embodiment, one or more treatment decision or clinical trial recruitment is undertaken based on the third set of output values.

In an embodiment, an intensified treatment is administered to one or more patients, based on the third set of output values.

In an embodiment, high-risk patients are selected for investigational therapy for a clinical trial, based on the third set of output values.

In an embodiment, a batch of microscopic images are obtained comprising tissue structures of one or more patients. A batch of macroscopic images comprising radiomic features of one or more patients are obtained. A first set of output values is generated by applying a first trained neural network and a first trained machine learning model to the batch of microscopic images. A second set of output values is generated by applying a second trained neural network and a second trained machine learning model to the batch of macroscopic images. A third set of output values is generated informative of the cancer prediction by applying a fully connected network to the first set of output values, the second set of output values, and a batch of electronic health record (EHR) data of one or more patients.

In an embodiment, a method develops a set of machine learning models for generating a cancer prediction for one or more prospective patients. A batch of images captured from one or more patients is obtained. A convolutional neural network model is trained by providing, as input, the batch of images until an improvement in output data between each epoch of training is less than a pre-defined threshold captured by a performance metric. A machine learning model is trained by providing, as input, extracted features from the batch of images until an improvement in output data between each epoch of training is less than a pre-defined threshold captured by a performance metric. The convolutional neural network and the machine learning model are locked.

In an embodiment, obtaining the batch of images comprises obtaining a batch of microscopic training images comprising tissue structures of one or more patients and obtaining a batch of macroscopic training images comprising radiomic features of the one or more patients. Training the convolutional neural network and training the machine learning model comprises training a first neural network and a first machine learning model by using the batch of microscopic images until an improvement in output data between each epoch of training is less than a pre-defined threshold captured by a performance metric and training a second neural network and a second machine learning model by using the batch of macroscopic images until an improvement in output data between each epoch of training is less than a pre-defined threshold captured by a performance metric. A first set of output features from each epoch of training in the first neural network and the first machine learning model is generated. A second set of output features from each epoch of training in the second neural network and the second machine learning model is generated. A batch of electronic health record (EHR) data is obtained. A fully connected network is trained by using the first set of output features, the second set of output features, and the batch of EHR data until an improvement in output data between each epoch of training is less than a pre-defined threshold captured by a performance metric.

BRIEF DESCRIPTION OF THE DRAWINGS

These and other features, aspects, and advantages of the present invention will become better understood with regard to the following description and accompanying drawings. It is noted that wherever practicable similar or like reference numbers may be used in the figures and may indicate similar or like functionality. For example, a letter after a reference numeral, such as "trained convolutional neural network 220A," indicates that the text refers specifically to the element having that particular reference numeral. A reference numeral in the text without a following letter, such as "trained convolutional neural network 220," refers to any or all of the elements in the figures bearing that reference numeral (e.g., "trained convolutional neural network 220" in the text refers to reference numerals "trained convolutional neural network 220A" and/or "trained convolutional neural network 220B" in the figures).

FIG. 2B illustrates a flow process for generating a cancer prediction, in accordance with an embodiment.

FIG. 3B illustrates a flow process for performing training of a multimodal framework, in accordance with an embodiment.

FIG. 9 illustrates an example training phase of a multimodal framework based on histopathology data in prostate cancer.

FIG. 11 is a set of plots illustrating multimodal risk stratification associated with example data relating to the described multimodal framework.

FIG. 13 is a table illustrating example hazard ratio data associated with the described multimodal framework.

DETAILED DESCRIPTION

I. System Environment Overview

Figure 1A:
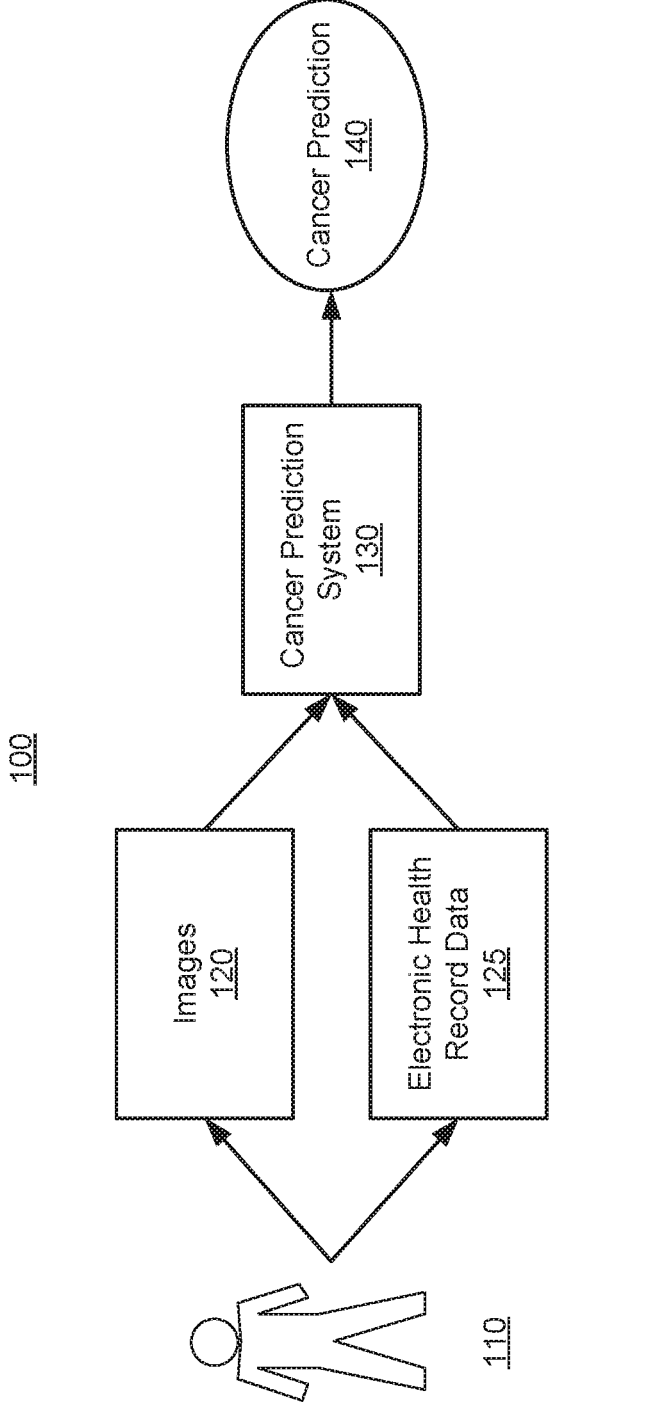
FIG. 1A depicts a system environment overview for predicting cancer, in accordance with an embodiment.

FIG. 1A depicts a system environment overview 100 for predicting cancer, in accordance with an embodiment. The system environment 100 provides context in order to introduce a subject (or patient) 110, images 120, electronic health record data 125, and a cancer prediction system 130 for generating a cancer prediction 140 for the subject 110. The subject or patient may encompass, for example, a cell, tissue, or organism, human or non-human, whether in vivo, ex vivo, or in vitro, male or female. The system environment overview 100 may include one or more subjects 110 for whom a cancer prediction 140 is generated. For example, although FIG. 1A depicts one subject 110 for whom a cancer prediction 140 is generated, in various embodiments, the system environment 100 includes two or more subjects such that that cancer prediction system 130 generates cancer predictions 140 for the two or more subjects (e.g., a cancer prediction for each subject).

In various embodiments, the subject 110 is healthy. For example, the subject is not previously diagnosed with cancer or is not suspected of having cancer. Thus, the methods for cancer predictions described herein can be beneficial for early identification of cancer in the healthy subject. In various embodiments, the subject was previously diagnosed with a cancer. In particular embodiments, the subject was previously diagnosed with a prostate cancer. In particular embodiments, the subject was previously diagnosed with a lung cancer. In particular embodiments, the subject was previously diagnosed with pancreatic cancer.

In various embodiments, the subject 110 was previously diagnosed with a cancer, such as prostate cancer, lung cancer, or pancreatic cancer. Therefore, the methods for cancer predictions can be beneficial for determining whether the subject is likely to experience cancer progression or experience a recurrence of cancer within a time period.

In some embodiments, based on the prediction, a therapeutic intervention can be selected for treating the cancer of the subject. In various embodiments, subjects predicted to develop cancer or experience a cancer recurrence within a time period can be administered treatments, examples of which are described herein. In various embodiments, subjects predicted to develop cancer or experience a cancer recurrence within a time period are selected to be enrolled in a clinical trial.

Referring to FIG. 1A, the images 120 and electronic health record data 125 includes one or more images from the subject 110 and health record data determined from the subject 110. In various embodiments, the images 120 and electronic health record data 125 can be captured or determined from a test sample of the subject 110. In various embodiments, the images 120, electronic health record data 125, and/or the sample can be obtained by a third party. e.g., a medical professional. Examples of medical professionals include physicians, emergency medical technicians, nurses, first responders, psychologists, phlebotomist, medical physics personnel, nurse practitioners, surgeons, dentists, and any other obvious medical professional as would be known to one skilled in the art.

In various embodiments, the test sample obtained from the subject 110 is a tissue biopsy. In various embodiments, the test sample undergoes tissue preparation and a hematoxylin and eosin (H&E) stain such that an H&E image of the tissue can be captured. For example, a conventional H&E staining process can involve: 1) preserving the tissue biopsy in formalin or paraffin embedding, 2) slicing tissue into thin sections (e.g., 4-5 μm in thickness), 3) removing embedding medium and rehydrating in xylene, ethanol, and deionized water), 4) staining (e.g., antibody staining) for a target, 5) counterstaining using hematoxylin, and 6) mounting of stained tissue slice on a slide for imaging.

In various embodiments, the image and/or the sample can be obtained in a hospital setting or a medical clinic. In various embodiments, the image and/or the sample can be captured using an imaging device, such as a mobile imaging device. In various embodiments, the images 120 include electronic images and/or data. In various embodiments, the images 120 include printed images and/or data. In various embodiments, the images 120 include scanned images and/or data. In various embodiments, the images 120 include one or more macroscopic images. In various embodiments, the macroscopic images include radiomic data (e.g., computed tomography (CT) or Positron emission tomography (PET)) of the subject 110. In various embodiments, the images 120 include one or more microscopic images. In various embodiments, the microscopic images comprise histopathology data such as hematology-eosin (H&E) images. In various embodiments, the images 120 include one or more histopathology data (e.g., hematology-eosin (H&E) images) of the subject 110. In particular embodiments, the images 120 include both microscopic images and macroscopic images. In particular embodiments, the images 120 include both H&E images and radiomic images.

In various embodiments, the images 120 are obtained from a clinical trial. In various embodiments, the images 120 are obtained from a real-world database (e.g., a hospital). In various embodiments, the images 120 are obtained from a public data set (e.g., a library).

Obtaining the microscopic images, macroscopic images, or other images may involve capturing the images of a subject or from a sample obtained from a subject. Obtaining the images may include capturing one or more images and/or receiving one or more images (e.g., from a third party that has performed the steps of capturing the one or more images from the subject or from a sample obtained from the subject). The one or more images can be obtained via a variety of ways including from a storage memory. Obtaining the images can include obtaining images that are each captured from a subject at a single timepoint (e.g., a single patient visit) or different points. Obtaining the images can furthermore include having (e.g., instructing) a third party perform the steps for obtaining the one or more images.

In various embodiments, the electronic health record (EHR) data 125 includes EHR data of the subject 110. In various embodiments, the EHR data 125 includes clinical data of a subject 110 such as age, sex, ethnicity, smoking history, geographical location, pollution exposure, lab tests and/or family history of cancers. In various embodiments, genomic data can be integrated into the EHR data (e.g., to enhance clinical diagnosis, precision medicine, and/or the treatment of genetic disorders).

Generally, the cancer prediction system 130 analyzes one or more images 120 and/or electronic health record data 125 captured from the subject 110 and generates the cancer prediction 140 for the subject 110 using multiple trained models. In various embodiments, the cancer prediction 140 determined by the cancer prediction system 130 is a predicted risk of cancer progression for the subject 110. For example, the cancer prediction 140 is a value indicating whether the subject 110 is predicted to experience cancer progression within a time period (e.g., within 1 year, within 3 years, or within 5 years) from a date that the images were captured from the subject 110. In various embodiments, the cancer prediction 140 is a value indicating a likelihood of therapeutic resistance in the subject 110 within a period of time. In particular embodiments, the cancer prediction 140 is a composite risk index indicating predicted cancer progression risk. In particular embodiments, a report that includes the composite risk index can be sent to an end-user (e.g., a healthcare professional or a patient) to assess the patient's risk of cancer progression.

In particular embodiments, the cancer prediction 140 includes a prediction for cancer. In particular embodiments, the cancer prediction 140 includes a prediction for prostate cancer. In particular embodiments, the cancer prediction 140 includes a prediction for lung cancer. In particular embodiments, the cancer prediction 140 includes a prediction for pancreatic cancer.

In various embodiments, a recommended intervention is undertaken based on the cancer prediction 140 for the subject 110. In various embodiments, the recommended intervention includes one or more treatment decisions. For example, if the cancer prediction system 130 determines that the subject 110 is likely to develop a cancer within M years, the cancer prediction 140 can include a recommended intervention to delay or prevent the rapid onset of the cancer over the M years. In various embodiments, one or more clinical trial recruitment is undertaken based on the cancer prediction 140 for the subject 110. As another example, if the cancer prediction system 130 determines that the subject 110 is likely to experience cancer progression within M years, the cancer prediction 140 can include a recommended intervention to slow the cancer progression over the M years.

The cancer prediction system 130 can include one or more computers, embodied as a computer system 400 as discussed below with respect to FIG. 4. Therefore, in various embodiments, the steps described in reference to the cancer prediction system 130 are performed in silico.

In various embodiments, different parties may obtain the images 120 and health record data 125 and implement the cancer prediction system 130. For example, a first party obtains the images 120 and/or electronic health record data 125 for the subject 110 and then provides the one or more images 120 and/or electronic health record data 125 to a second party which implements the cancer prediction system 130 to determine a cancer prediction 140. In some embodiments, the same party obtains the images 120 and electronic health record data 125 and implements the cancer prediction system 130.

Figure 1B:
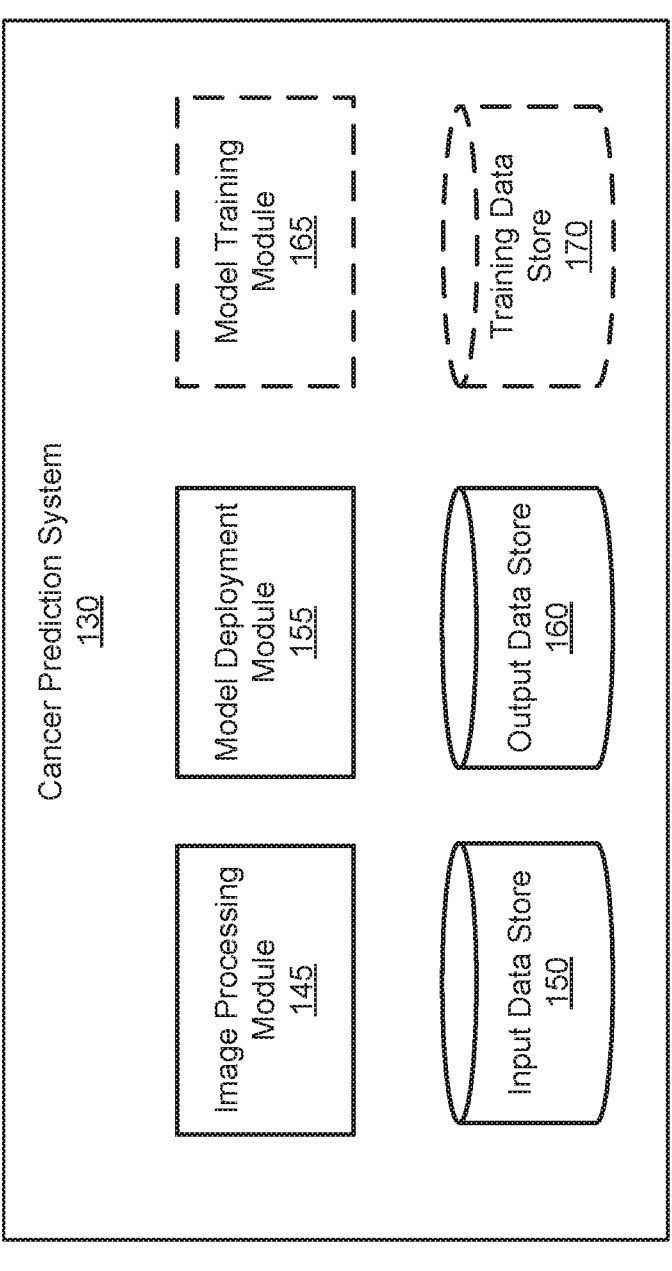
FIG. 1B illustrates a block diagram of the cancer prediction system, in accordance with an embodiment.

Reference is now made to FIG. 1B which depicts a block diagram of the cancer prediction system 130, in accordance with an embodiment. Here, the cancer prediction system 130 includes an image processing module 145, an input data store 150, a model deployment module 155, an output data store 160, a model training module 165, and a training data store 170. In various embodiments, the cancer prediction system 130 can be configured differently with additional or fewer modules. For example, a cancer prediction system 130 need not include the input data store 150. As another example, the cancer prediction system 130 need not include the model training module 165 or the training data store 170 (as indicated by their dotted lines in FIG. 1B), and instead, the model training module 165 and training data store 170 are employed by a different system and/or party.

The components of the cancer prediction system 130 are hereafter described in reference to two phases: 1) a training phase and 2) a deployment phase. More specifically, the training phase refers to the building, developing, and training of one or more models using training data, such as training images captured from training individuals (e.g., individuals who are known to develop or not develop cancer within a period of time). Therefore, the models are trained using the training data such that during the deployment phase, implementation of the models by the model deployment module 155 enables the generation of a cancer prediction (e.g., cancer prediction 140 in FIG. 1A).

Generally, the image processing module 145 processes (e.g., pre-process, identify region of interest, or extract features) images captured from subjects or training images captured from training individuals. The training images may include images (e.g., histology image or radiology image) captured from an individual that is used to train a machine learning model, e.g., a convolutional neural network or other machine learning model as described herein. In particular embodiments, the image processing module 145 pre-processes images or training images by removing artifacts in the images or training images, resampling images or training images to a uniform resolution, normalizing imaging intensity in the images or training images, and/or sub-dividing images or training images for efficient processing (e.g., tiling, batching). In particular embodiments, the image processing module 145 defines regions of interest (ROI) in images or training images by manually selecting tumor regions, applying automatic contouring algorithms, or combinations thereof. In particular embodiments, the image processing module 145 extracts interpretable features from the images or training images, such as cell count, cell size, sell shape, tumor size, tumor roundness, interpretable radiomic or textural features, or other interpretable radiomic and textural features. Here, the image processing module 145 may implement an image feature extraction algorithm to extract the interpretable features. Further description of example feature extraction algorithms are found in Yip SS. et al.: Associations Between Radiologist-Defined Semantic And Automatically Computed Radiomic Features In Non-Small Cell Lung Cancer, Scientific Reports 7:3519, 2017, and Lu C. et al.: Nuclear shape and orientation features from H&E images predict survival in early-stage estrogen receptor-positive breast cancers, Laboratory Investigation, 98(11):1438-1448, 2018, each of which is hereby incorporated by reference in its entirety.

In various embodiments, the image processing module 145 provides interpretable features of the processed images as well as the processed images to the model deployment module 155 for deploying models. In various embodiments, the image processing module 145 provides interpretable features of the processed training images as well as the processed images to the model training module 165 for training models.

The input data store 150 stores images and/or health record data for one or more subjects (e.g., subject 110 in FIG. 1A) for the image processing module 145 to process.

The model deployment module 155 implements multiple models to analyze one or more images captured from a subject (e.g., subject 110 in FIG. 1A) and processed by the image processing module 145 to generate a cancer prediction for the subject 110.

In various embodiments, the model deployment module 155 implements at least one convolutional neural network (CNN) and one machine learning model (MLM) for analyzing images. In various embodiments, the model deployment module 155 implements at least one convolutional neural network (CNN) and one machine learning model (MLM) for analyzing microscopic images. The CNN may include various types of models that analyze images and detects features, such as non-interpretable features, of the images. Generally, image features need not be extracted prior to the application of the CNN. The MLM may include various types of models that analyzes features, such as interpretable features, that are extracted from images, examples of which are described in further detail herein. In various embodiments, the model deployment module 155 implements at least one CNN and one MLM for analyzing macroscopic images. In particular embodiments, the model deployment module 155 implements two convolutional neural networks (CNNs) and two machine learning models (MLMs) for analyzing microscopic images and macroscopic images. In various embodiments, the model deployment module 155 implements at least a fully connected network (FCN) for analyzing the output from the CNN(s) and MLM(s) to generate or determine cancer predictions. In various embodiments, the CNN, MLM, and FCN included in the model deployment module 155 are previously trained and locked for deployment.

In various embodiments, the models deployed by the model deployment module 155 can predict whether a subject is likely to develop cancer in the next year. In various embodiments, the models in the model deployment module 155 can be implemented to predict whether a subject is likely to develop cancer in the next year. In various embodiments, the models in the model deployment module 155 can be implemented to predict whether a subject is likely to develop cancer in the next 3 years. In various embodiments, the models in the model deployment module 155 can be implemented to predict whether a subject is likely to develop cancer in the next 5 years. In various embodiments, the models in the model deployment module 155 can be implemented to predict whether a subject is likely to develop cancer within a M time period. In various embodiments, M is any of 6 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years.

The output data store 160 stores data (e.g., quantitative values) informative of cancer predictions for one or more subjects generated from the model deployment module 155.

The model training module 165 trains one or more models (e.g., CNNs and MLMs) using training data derived from training individuals and saved in the training data store 170. In various embodiments, training individuals refer to individuals for whom there is a known outcome. For example, training individuals can include individuals who are known to either experience or not experience disease progression within M years. As another example, training individuals can include individuals who are known to either experience or not experience cancer therapeutic resistance.

In various embodiments, the training data includes one or more raw images captured from the training individuals. In various embodiments, the training data includes engineered features from one or more training images captured from the training individuals, wherein the engineered features are obtained by the image processing module 145 by analyzing one or more raw training images. In various embodiments, the engineered features include interpretable features. In various embodiments, the engineered features include non-interpretable features. The non-interpretable features may include sophisticated features that cannot be readily explained or interpreted by humans (e.g., experts) but can be identified by the convolutional neural network. Examples of non-interpretable features include hidden or subtle features that are informative of certain biological processes (e.g., cancer progression or resistance to therapy).

In various embodiments, the training data further includes electrical health record data from the training individuals. In various embodiments, the model training module 165 trains one or more CNN, one or more MLM, and at least one FCN.

In various embodiments, the model training module 165 trains at least one convolutional neural network (CNN) and one machine learning model (MLM) using microscopic training images. In various embodiments, the model training module 165 trains at least one CNN and one MLM using macroscopic training images. In particular embodiments, the model training module 165 trains two CNNs and two MLMs using microscopic training images and macroscopic training images. In various embodiments, the model training module 165 further trains at least a fully connected network (FCN) based on the output generated from the CNN(s) and MLM (s).

In various embodiments, the components of the cancer prediction system 130 are applied during one of the training phase and the deployment phase. For example, the model training module 165 and training data store 170 are applied during the training phase to train a model. Additionally, the model deployment module 155 is applied during the deployment phase. In various embodiments, the components of the cancer prediction system 130 can be performed by different parties depending on whether the components are applied during the training phase or the deployment phase. In such scenarios, the training and deployment of the prediction model are performed by different parties. For example, the model training module 165 and training data store 170 applied during the training phase can be employed by a first party (e.g., to train a model) and the model deployment module 155 applied during the deployment phase can be performed by a second party (e.g., to deploy the model). Training models and deploying models are described in further detail below.

II. Methods for Generating Cancer Prediction

Figure 2A:
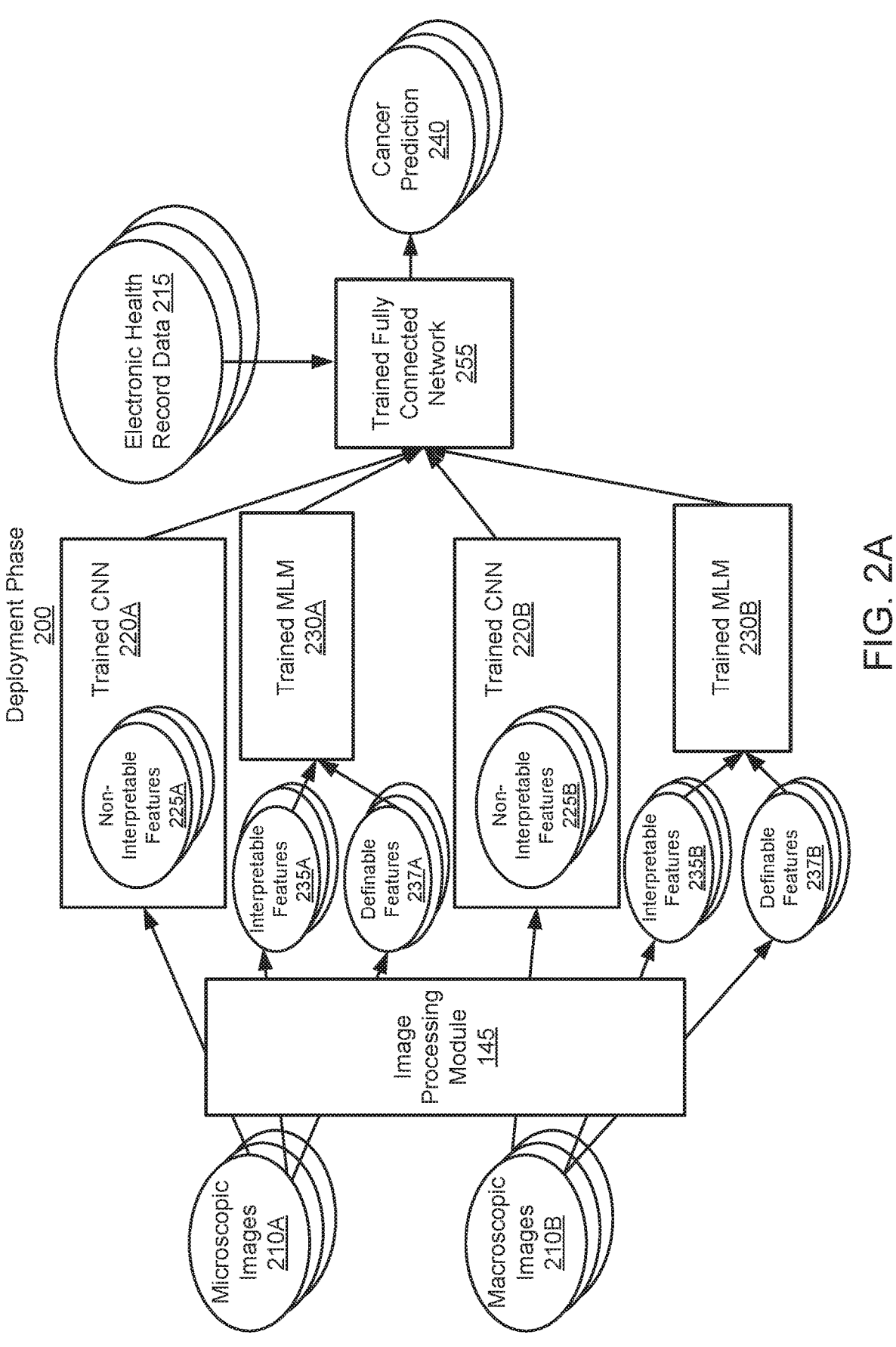
FIG. 2A illustrates a block diagram for generating a cancer prediction, in accordance with an embodiment.

Embodiments described herein include methods for generating a cancer prediction for a subject by applying one or more trained models to analyze microscopic images, macroscopic images, and/or EHR data. Such methods can be performed by the cancer prediction system 130 described in FIG. 1B. Reference will further be made to FIG. 2A, which depicts an example block diagram of a deployment phase 200 for generating a cancer prediction for a subject for uses such as recommended intervention or clinical trial enrollment, in accordance with an embodiment.

As shown in FIG. 2A, a deployment pipeline includes the deployment of four different models (e.g., trained convolutional neural network (CNN) 220A, trained machine learning model 230A, trained convolutional neural network CNN 220B, and trained machine learning model 230B. Two of the models (e.g., trained CNN 220A and trained MLM 230A) are deployed to analyze and/or identify features of a first set of images (e.g., microscopic images 210A). Two of the models (e.g., trained CNN 220B and trained MLM 230B) are deployed to analyze and/or identify features of a second set of images (e.g., macroscopic images 210B). Generally, the deployment of both a trained CNN and a trained MLM to analyze and/or identify features of a set of images enables broader analysis of various image features than the deployment of any single model. For example, a trained MLM analyzes interpretable features which are extracted from images. Additionally, the trained CNN can identify and analyze non-interpretable features, which represent sophisticated features that are detected by the CNN and therefore, may supplement and/or be different from the interpretable features. Thus, analyzing both the interpretable features and non-interpretable features using the two models enables the subsequent generation of improved cancer predictions.

As shown in FIG. 2A, a microscopic image 210A and/or a macroscopic image 210B from a subject (e.g., subject 110 in FIG. 1A) are obtained and stored in a input data store (e.g., input data store 150 in FIG. 1B). In various embodiments, the microscopic image 210A includes histology images that captures one or more cancer cells, lymphocytes, stromal cells, and epithelial cells. In various embodiments, the macroscopic image 210B includes radiology images that captures one or more tumor areas, surrounding areas in proximity to the tumor area, and lymph nodes.

The image processing module 145 processes images (e.g., microscopic image 210A and the macroscopic image 210B) for deploying models in the model deployment module (e.g., model deployment module 155 in FIG. 1B). In various embodiments, the image processing module 145 implements an image analysis algorithm to process images (e.g., microscopic image 210A and the macroscopic image 210B).

Generally, the image processing module 145 provides the microscopic images 210A to the trained convolutional neural network (CNN) 220A. Here, the trained CNN 220A analyzes the microscopic images and identifies non-interpretable features 225A for generating an output. The image processing module 145 processes microscopic images 210A and extracts interpretable features 235A and definable features 237A that are provided to a trained MLM 230A. In various embodiments, the interpretable features 235A comprise one or more cell counts, cell sizes, tumor sizes, tumor roundness, tumor compactness, tumor cell density, level of tumor infiltrating lymphocyte. The definable features may include features that cannot be readily interpreted or explained by humans (e.g., experts) but can be defined using formulas. An example of a definable feature includes definable radiomic features, such as gray-level co-occurrence matrices (GLCM)-entropy. Additionally, the image processing module 145 provides the macroscopic images 210B to the trained convolutional neural network (CNN) 220B. Here, the trained CNN 220B analyzes the macroscopic images and identifies non-interpretable features 225B for generating an output. The image processing module 145 processes macroscopic images 210B and extracts interpretable features 235B and definable features 237B that are provided to a trained MLM 230B. In various embodiments, the interpretable features 235B comprise one or more cell counts, cell sizes, tumor sizes, tumor roundness, tumor compactness, tumor cell density, level of tumor infiltrating lymphocyte.

In various embodiments, each of the non-interpretable features 225A, the interpretable features 235A, or the definable features 237A includes at least 2 features from microscopic image 210A. In various embodiments, each of the non-interpretable features 225A, the interpretable features 235A, or the definable features 237A includes at least 3, at least 4, at least 5, at least 6, at least 7, at least 8, at least 9, or at least 10 features from microscopic image 210A. In various embodiments, each of the non-interpretable features 225A, the interpretable features 235A, or the definable features 237A includes at least 15, at least 20, at least 25, at least 30, at least 35, at least 40, or at least 45 features from microscopic image 210A. In various embodiments, each of the non-interpretable features 225A, the interpretable features 235A, or the definable features 237A includes at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, or at least 1000 features from microscopic image 210A.

In various embodiments, each of the non-interpretable features 225B, the interpretable features 235B, or the definable features 237B includes at least 2 features from macroscopic image 210B. In various embodiments, each of the non-interpretable features 225B, the interpretable features 235B, or the definable features 237B includes at least 3, at least 4, at least 5, at least 6, at least 7, at least 8, at least 9, or at least 10 features from microscopic image 210B. In various embodiments, each of the non-interpretable features 225B, the interpretable features 235B, or the definable features 237B includes at least 15, at least 20, at least 25, at least 30, at least 35, at least 40, or at least 45 features from macroscopic image 210B. In various embodiments, each of the non-interpretable features 225B, the interpretable features 235B, or the definable features 237B includes at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, or at least 1000 features from macroscopic image 210B.

Referring to FIG. 2A, the trained CNN 220A determines and analyzes the non-interpretable features 225A of the microscopic image 210A. The trained MLM 230A analyzes the interpretable features 235A and the definable features 237A of the microscopic image 210A. The trained CNN 220B determines and analyzes the non-interpretable features 225B of the macroscopic image 210B. The trained MLM 230B analyzes the interpretable features 235B and the definable features 237B of the macroscopic image 210B.

As shown in FIG. 2A, the output generated from each of the trained CNN 220A, MLM 230A, CNN 220B, and MLM 230B, as well as the EHR data 215 are provided as inputs to a trained fully connected network (FCN) 255. In various embodiments, the output generated from each of the trained CNN 220A, MLM 230A, CNN 220B, and MLM 230B, as well as the EHR data 215 are concatenated prior to being provided as input into the trained FCN 255. In various embodiments, the concatenation involves arranging the output generated from each of the trained CNN 220A, MLM 230A, CNN 220B, and MLM 230B, and the EHR data 215 in an input vector. Thus, the input vector can be provided as input to the trained FCN 255.

As shown in FIG. 2A, the output generated from each of the trained CNN 220A, MLM 230A, CNN 220B, and MLM 230B, as well as the EHR data 215 are provided as input to a trained fully connected network (FCN) 255. In various embodiments, the output generated from each of the trained CNN 220A, MLM 230A, CNN 220B, and MLM 230B, as well as the EHR data 215 are concatenated prior to providing as input to the trained FCN 255. In various embodiments, the concatenation involves arranging the output generated from each of the trained CNN 220A, MLM 230A, CNN 220B, and MLM 230B, and the EHR data 215 in an input vector. Thus, the input vector can be provided as input to the FCN 255. In various embodiments, the trained FCN 255 is any one of a neural network, random forest, or support vector machine.

Reference is now made to FIG. 2B, which depicts a flow process 250 for deploying a set of models for generating cancer prediction for a subject (e.g. a patient), in accordance with a second embodiment. In particular embodiments, the subject is a patient diagnosed with cancer. In various embodiments, the flow diagram 250 is used for one category of images, such as microscopic images. In various embodiments, the flow diagram 250 is used for one category of images, such as microscopic images. In various embodiments, the flow diagram 250 includes additional steps (e.g., steps similar to steps 260, 270, and 280) to analyze more categories of images respectively. For example, if the images include two categories of images such as microscopic images and macroscopic images, the flow diagrams 250 may include two sets of CNN and MLM, where each set of CNN and MLM follow steps 260, 270, and 280 to analyze each of the two categories of images, and to provide a first, a second, a third, and a fourth set of output values to the FCN in step 290.

At step 260, a first batch of images are obtained, where the first batch of images are captured from one or more patients. In various embodiments, the first batch of images are one category of images or a subset of the category of images. In particular embodiments, the first batch of images are microscopic images. In particular embodiments, the first batch of images are macroscopic images.

At step 270, a first set of output values is generated by providing, as input, the first batch of images to a first CNN (e.g., trained CNN 220A, or trained CNN 220B in FIG. 2A). In various embodiments, the first CNN identifies one or more non-interpretable features from the first batch of images to generate the first set of output values. In various embodiments, the first CNN has been fully trained.

Figure 3A:
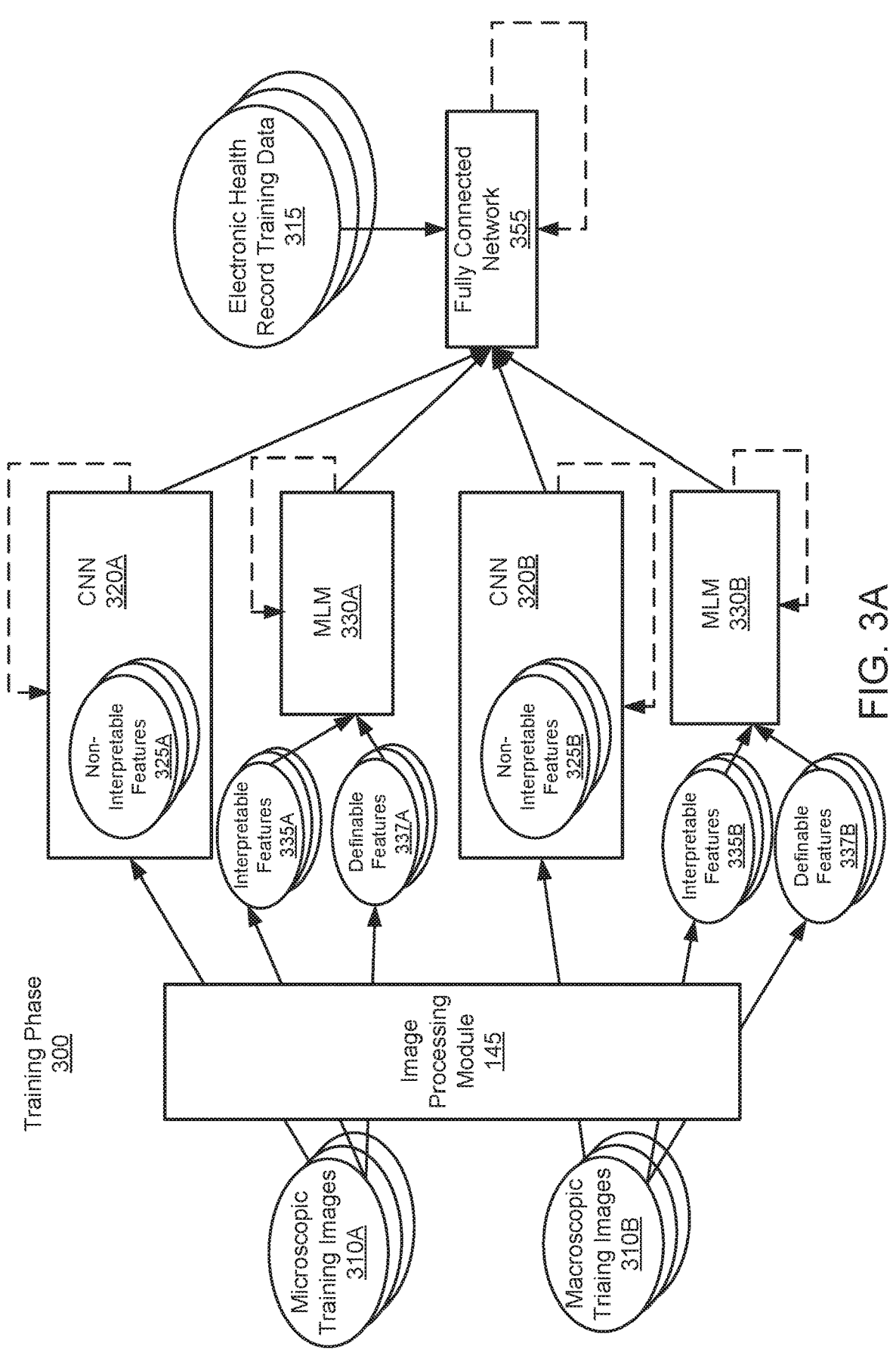
FIG. 3A illustrates a block diagram for performing training of a multimodal framework, in accordance with an embodiment.

At step 280, a second set of output values is generated by providing, as input, interpretable and machine learned features of the first batch of images to a first MLM (e.g., MLM 230A or MLM 230B in FIG. 3A). In various embodiments, one or more interpretable and machine learned features from the first batch of images are provided as input to the first MLM to generate the second set of output values. In various embodiments, the first MLM has been fully trained.

At step 290, a third set of output values informative of the cancer prediction is generated by providing, as input, at least the first set of output values and the second set of output values to a fully connected network (FCN).

In various embodiments, as described above, the steps 260, 270, and 280 further include deploying one or more additional CNNs and MLMs based on additional categories of images provided to generate additional sets of output values. For example, steps 260, 270, and 280 may further include deploying a second CNN and a second MLM based on a second batch of images to generate a fourth and fifth set of output values. Thus, at step 290, a third set of output values informative of the cancer prediction is generated by providing, as input, at least the first, the second, the fourth, and the fifth set of output values to a fully connected network (FCN).

III. Training Models in a Cancer Prediction System

FIG. 3A depicts an block diagram for performing training of a multimodal framework, in accordance with an embodiment. The training phase 300 includes at least one microscopic training image 310A and/or a macroscopic training image 310B that are obtained and stored in a training data store (e.g., training data store 170 in FIG. 1B). In various embodiments, the microscopic training images 310A include histology images that capture one or more cancer cells, lymphocytes, stromal cells, and/or epithelial cells from a subject (e.g., a patient). In various embodiments, the macroscopic training images 310B include radiology images that capture one or more tumor areas, surrounding areas in proximity to the tumor area, and/or lymph nodes from a patient.

Here, FIG. 3A differs from FIG. 2A in that FIG. 3A includes models for training based on training images, while FIG. 2 includes using models that have been trained (e.g. trained in the training phase 300). In various embodiments, at least part of the subjects (e.g., patients) involved in the training phase 300 are different from prospective subjects (e.g., patients) involved in the deployment phase 200. For example, the training images may be obtained from some patients who are not involved in images used in the deployment. In various embodiments, at least part of the subjects (e.g., patients) involved in the training phase 300 are the same as prospective subjects (e.g., patients) involved in the deployment phase 200. For example, the training images may be obtained from some patients who are involved in images used in the deployment.

Referring to FIG. 3A, the image processing module 145 processes training images (e.g., microscopic training image 310A and the macroscopic training image 310B) such that the model training module (e.g., model training module 165 in FIG. 1B) can use at least the processed training images to train the models. In various embodiments, the model training module 165 implements an image analysis algorithm to processes training images. In various embodiments, the training images are obtained from a clinical trial. In various embodiments, the training images are obtained from a real-world database (e.g., a hospital). In various embodiments, the training images are obtained from a public data set (e.g., a library).

Generally, the processed microscopic image includes non-interpretable features 325A for training a CNN 320A. The processed microscopic image includes interpretable features 335A and definable features 337A for training a MLM 330A. The processed macroscopic image includes non-interpretable features 325B for training a CNN 320B. The processed macroscopic image includes interpretable features 335B and definable features 337B for training a MLM 330B.

In various embodiments, the CNN 320A identifies non-interpretable features 325A from the microscopic training images 310A. In various embodiments, the MLM 330A identifies definable features 337A from the microscopic training images 310A. In various embodiments, the CNN 320B identifies non-interpretable features 325B from the macroscopic training images 310B. In various embodiments, the MLM 330B identifies definable features 337B from the macroscopic training images 310B.

In various embodiments, interpretable features 335A are extracted by the image processing module 145 to provide as input for training of the MLM 330A. In various embodiments, the interpretable features 335B are extracted by the image processing module 145 to provide as input for training of the MLM 330B. In various embodiments, the interpretable features 335A comprise one or more cell counts, cell size, tumor sizes, tumor roundness, tumor compactness, tumor cell density, level of tumor infiltrating lymphocyte. In various embodiments, the interpretable features 335B comprise one or more cell counts, cell size, tumor sizes, tumor roundness, tumor compactness, tumor cell density, level of tumor infiltrating lymphocyte.

In various embodiments, the definable features 337A or 337B include features that can be defined by a formula but cannot be readily interpreted or explained by humans, even experts (e.g., pathologists or radiologists). For example, the definable features 337A can include textual features from the microscopic training images 310A. For example, the definable features 337B can include textual features from the macroscopic training images 310B.

In various embodiments, each of the non-interpretable features 325A, the interpretable features 335A, or the definable features 337A includes at least 2 features from microscopic training image 310A. In various embodiments, each of the non-interpretable features 325A, the interpretable features 335A, or the definable features 337A includes at least 3, at least 4, at least 5, at least 6, at least 7, at least 8, at least 9, or at least 10 features from the microscopic training image 310A. In various embodiments, each of the non-interpretable features 325A, the interpretable features 335A, or the definable features 337A includes at least 15, at least 20, at least 25, at least 30, at least 35, at least 40, or at least 45 features from microscopic training image 310A. In various embodiments, each of the non-interpretable features 325A, the interpretable features 335A, or the definable features 337A includes at least 100 features, at least 150 features, at least 200 features, at least 250 features, at least 300 features, at least 350 features, at least 400 features, at least 450 features, at least 50) features, at least 550 features, at least 600 features, at least 650 features, at least 700 features, at least 750 features, at least 800 features, at least 850 features, at least 900 features, at least 950 features, or at least 1000 features from microscopic training image 310A.

In various embodiments, each of the non-interpretable features 325B, the interpretable features 335B, or the definable features 337B includes at least 2 features from macroscopic training image 310B. In various embodiments, each of the non-interpretable features 325B, the interpretable features 335B, or the definable features 337B includes at least 3, at least 4, at least 5, at least 6, at least 7, at least 8, at least 9, or at least 10 features from macroscopic training image 310B. In various embodiments, each of the non-interpretable features 325B, the interpretable features 335B, or the definable features 337B includes at least 15, at least 20, at least 25, at least 30, at least 35, at least 40, or at least 45 features from macroscopic training image 310B. In various embodiments, each of the non-interpretable features 325B, the interpretable features 335B, or the definable features 337B includes at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, or at least 1000 features from macroscopic training image 310B.

Referring to FIG. 3A, the CNN 320A analyzes the non-interpretable features 325A of the microscopic training image 310A. The MLM 330A analyzes the interpretable features 335A and the definable features 337A of the microscopic training image 310A. The CNN 320B analyzes the non-interpretable features 325B of the macroscopic training image 310B. The MLM 330B analyzes the interpretable features 335B and the definable features 337A of the macroscopic training image 310B.

The output generated from each of the CNN 320A, MLM 330A, CNN 320B, and MLM 330B, as well as EHR training data 315 are provided as input to train a connected network (FCN) 355. In various embodiments, the output generated from each of the CNN 320A, MLM 330A, CNN 320B, and MLM 330B, as well as the EHR training data 315 are concatenated prior to providing as input to the fully connected network (FCN) 355. In various embodiments, the concatenation involves arranging the output generated from one or more epochs of training of each of the CNN 320A, MLM 330A, CNN 320B, and MLM 330B, and the EHR training data 315 in an input vector. Thus, the input vector can be provided as input to the FCN 355. In various embodiments, the FCN 355 is any one of a neural network, random forest, or support vector machine.

As shown in FIG. 3A, as indicated by the dotted lines, the output values of the CNN 320A, MLM 330A, CNN 320B, MLM 330B, and FCN 355 may be used to train each respective model. In various embodiments, each of CNN 320A, MLM 330A, CNN 320B, MLM 330B, and FCN 355 is individually trained. Specifically, the output value of CNN 320A is used to further train CNN 320A. The output value of MLM 330A is used to further train MLM 330A. The output value of CNN 320B is used to further train CNN 320B. The output value of MLM 330B is used to further train MLM 330B. The output value of FCN 355 is used to further train FCN 355. For example, each of CNN 320A, MLM 330A, CNN 320B, MLM 330B, and FCN 355 can be individually and iteratively trained until an quantitative improvement in the output of each model between each epoch or between each iteration of training is less than a pre-defined threshold, or until a maximum number of iterations is reached.

In various embodiments, one or more of CNN 320A, MLM 330A, CNN 320B, MLM 330B, and FCN 355 are individually trained to minimize a loss function such that the output of each model is improved over successive training epochs. In various embodiments, the loss function is constructed for any of a least absolute shrinkage and selection operator (LASSO) regression, Ridge regression, or ElasticNet regression. In such embodiments, the dotted lines for the models shown in FIG. 3A can represent the backpropagation of a loss value calculated based on the loss function. Thus, one or more of the models are trained based on the backpropagated value such that the model improves its predictive capacity.

Reference is now made to FIG. 3B, which depicts a flow process 350 for performing training of a set of machine learning models (MLM), in accordance with a second embodiment. In various embodiments, the flow diagram 350 is used for one category of images, such as microscopic images. In various embodiments, the flow diagram 350 is used for one category of images, such as microscopic images. In various embodiments, the flow diagram 350 includes additional steps (e.g., steps similar to steps 360, 370, and 380) to analyze two or more categories of images respectively. For example, if the images include two categories of images such as microscopic images and macroscopic images, the flow diagram 350 may include two sets of CNN and MLM, where each set of CNN and MLM follow steps 360, 370, and 380 to analyze each of the two categories of images, and to provide a first, a second, a third, and a fourth set of output values to the FCN in step 390.

At step 360, a batch of images are captured from one or more patients. In various embodiments, the one or more patients are training individuals. In various embodiments, the first batch of images are one category of images or a subset of the category of images. In particular embodiments, the first batch of images are microscopic images. In particular embodiments, the first batch of images are macroscopic images.

At step 370, a CNN model (e.g. CNN 320A or 320B in FIG. 3A) is trained by providing, as input, the batch of images until an improvement in output data between each epoch of training is less than a pre-defined threshold.

At step 380, a MLM is trained by providing, as input, extracted features from the batch of images until an improvement in output data between each epoch of training is less than a pre-defined threshold. In various embodiments, the extracted features are interpretable features (e.g., interpretable features 335A or 335B in FIG. 3A). In various embodiments, the extracted features are definable features (e.g., definable features 337A or 337B in FIG. 3A). In various embodiments, steps 370 and 380 may be reversed such that the MLM is first trained followed by training of the CNN. In various embodiments, steps 370 and 380 may be performed in parallel.

At step 390, a fully connected network (FCN) is trained using output values obtained while training the CNN, output values obtained while training the MLM, and obtained electronic health record (EHR) data until an improvement in output data between each epoch of training is less than a pre-defined threshold.

In various embodiments, as described above, the steps 360, 370, and 380 further include performing training of one or more additional CNNs and MLMs based on additional categories of images provided to generate additional sets of output values. For example, steps 360, 370, and 380 may further include training a second CNN and a second MLM based on a second batch of images to generate additional output values. Thus, at step 390, the FCN is trained using output values obtained while training two CNNs, output values obtained while training two MLMs, and obtained electronic health record (EHR) data until an improvement in output data between each epoch of training is less than a pre-defined threshold.

At step 395, the CNN, the MLM, and/or the FCN that are trained in previous steps are locked for deployment (e.g., in deployment phase 200).

IV. Example Machine Learning Model and Convolutional Neural Networks

Embodiments described herein refer to the training and implementation of one or more models, such as machine learning models for analyzing interpretable features as well as convolutional neural networks for identifying and analyzing non-interpretable features.

In various embodiments, machine learning models for analyzing interpretable features can be any one of a regression model (e.g., linear regression, logistic regression, or polynomial regression), decision tree, random forest, gradient boosted machine learning model, support vector machine, Naïve Bayes model, or k-means cluster. In various embodiments, a machine learning model for analyzing interpretable features can be a neural network model (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, or deep bi-directional recurrent networks)). In particular embodiments, machine learning models for analyzing interpretable features are any one of a logistic regression model, cox proportional-hazards model, or random survival forest model.

In various embodiments, the machine learning model for analyzing interpretable features can be trained using a machine learning implemented method, such as any one of a linear regression algorithm, logistic regression algorithm, decision tree algorithm, support vector machine classification, Naïve Bayes classification. K-Nearest Neighbor classification, random forest algorithm, deep learning algorithm, gradient boosting algorithm, and dimensionality reduction techniques such as manifold learning, principal component analysis, factor analysis, autoencoder regularization, and independent component analysis, or combinations thereof. In various embodiments, the machine learning model is trained using supervised learning algorithms, unsupervised learning algorithms, semi-supervised learning algorithms (e.g., partial supervision), weak supervision, transfer, multi-task learning, or any combination thereof. In particular embodiments, the machine learning model is trained using a deep learning algorithm.

In various embodiments, a convolutional neural network for identifying and analyzing non-interpretable features includes one or more layers, each layer including one or more nodes. In various embodiments, different layers of the convolutional neural network can identify different features. For example, initial layers of the convolutional neural network can identify low-level features in images such as edges, bends, and points. As another example, subsequent layers of the convolutional neural network can detect higher-level features such as objects. Altogether, the different layers of the convolutional neural network enable identification of complex relationships and learning of hidden features in images that not interpretable by humans. In particular embodiments, the convolutional neural network is any one of VGGNet, ResNet, Inception, or other suitable models.

In various embodiments, machine learning models for analyzing interpretable features and convolutional neural networks for identifying and analyzing non-interpretable features may each include parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, node values in a decision tree, and coefficients in a regression model. The model parameters of the machine learning models and the convolutional neural networks are trained (e.g., adjusted) using the training data to improve the predictive capacity of the machine learning model.

V. Computer Implementation

The methods of the invention, including the methods of implementing models for generating cancer predictions, are, in some embodiments, performed on one or more computers.

For example, the building and deployment of a model can be implemented in hardware or software, or a combination of both. In one embodiment of the invention, a machine-readable storage medium is provided, the medium comprising a data storage material encoded with machine readable data which, when using a machine programmed with instructions for using said data, is capable of executing the training or deployment of models and/or displaying any of the datasets or results (e.g., a composite risk index) described herein. The invention can be implemented in computer programs executing on programmable computers, comprising a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high-level procedural or object-oriented programming language to communicate with a computer system. However, the programs can be implemented in assembly or machine language, if desired. In any case, the language can be a compiled or interpreted language. Each such computer program is preferably stored on a storage media or device (e.g., ROM, or magnetic diskette) readable by a general or special purpose programmable computer, for configuring and operating the computer w % ben the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM: hybrids of these categories such as magnetic/optical storage media; and cloud storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

In some embodiments, the methods of the invention, including the methods for generating a cancer prediction by implementing MLMs, CNNs, and FCNs, are performed on one or more computers in a distributed computing system environment (e.g., in a cloud computing environment). In this description, "cloud computing" is defined as a model for enabling on-demand network access to a shared set of configurable computing resources. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 4:
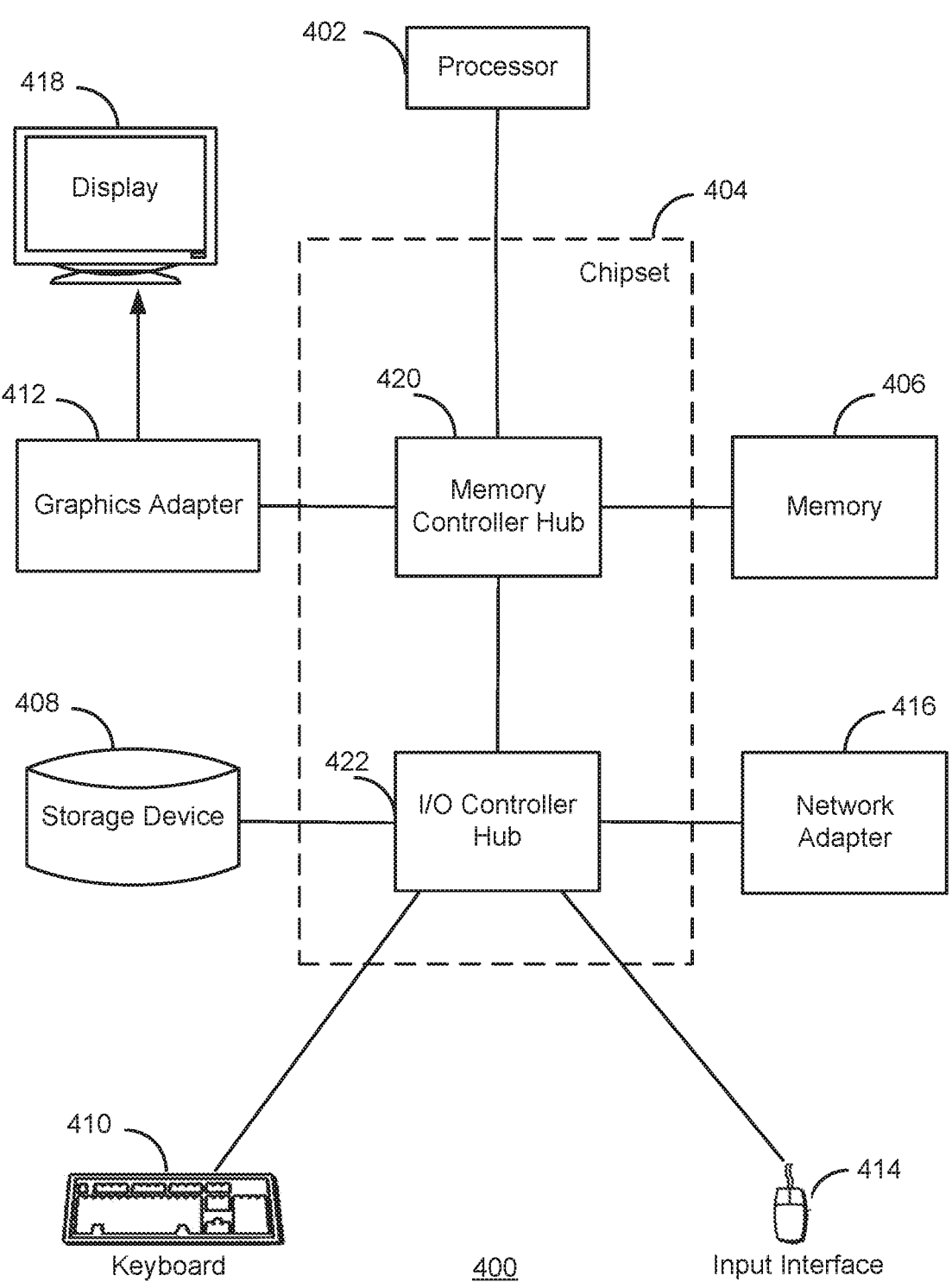
FIG. 4 illustrates an example computer for implementing the entities shown in FIGS. 1A, 1B, 2A, 2B, 3A, and 3B.

FIG. 4 illustrates an example computer for implementing the entities shown in FIGS. 1A, 1B, 2A, 2B, and 3. The computer 400 includes at least one processor 402 coupled to a chipset 404. The chipset 404 includes a memory controller hub 420 and an input/output (I/O) controller hub 422. A memory 406 and a graphics adapter 412 are coupled to the memory controller hub 420, and a display 418 is coupled to the graphics adapter 412. A storage device 408, an input device 414, and network adapter 416 are coupled to the I/O controller hub 422. Other embodiments of the computer 400 have different architectures.

The storage device 408 is a non-transitory computer-readable storage medium such as a hard drive, compact disk read-only memory (CD-ROM), DVD, or a solid-state memory device. The memory 406 holds instructions and data used by the processor 402. The input interface 414 is a touch-screen interface, a mouse, track ball, or other type of pointing device, a keyboard, or some combination thereof, and is used to input data into the computer 400. In some embodiments, the computer 400 may be configured to receive input (e.g., commands) from the input interface 414 via gestures from the user. The network adapter 416 couples the computer 400 to one or more computer networks.

The graphics adapter 412 displays images and other information on the display 418. In various embodiments, the display 418 is configured such that the user may (e.g., radiologist, oncologist, pulmonologist) may input user selections on the display 418 to, for example, initiate cancer prediction for a patient, order any additional exams or procedures and/or set parameters for the models. In one embodiment, the display 418 may include a touch interface. In various embodiments, the display 418 can show one or more cancer predictions for a subject. Thus, a user who accesses the display 418 can inform the subject of the cancer prediction that is predicted for the subject.

The computer 400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 408, loaded into the memory 406, and executed by the processor 402.

The types of computers 400 used by the entities of FIG. 1A or 1B can vary depending upon the embodiment and the processing power required by the entity. For example, the cancer prediction system 130 can run in a single computer 400 or multiple computers 400 communicating with each other through a network such as in a server farm. The computers 400 can lack some of the components described above, such as graphics adapters 412, and displays 418.

VI. Systems

Further disclosed herein are systems for implementing MLMs, CNNs, and FCNs for generating a cancer prediction. In various embodiments, such a system can include at least the cancer prediction system 130 described above in FIG. 1A. In various embodiments, the cancer prediction system 130 is embodied as a computer system, such as a computer system with example computer 400 described in FIG. 4.

The computer system implements, in silico, models to analyze the images and/or electronic health record data, and to generate a cancer prediction (e.g., a composite risk index) for the subject. In the clinical or user environment, the framework can be deployed on the cloud or locally.

VII. Cancers and Example Therapeutics

Methods described herein involve implementing convolutional neural networks and machine learning models for generating cancer predictions for subjects. In various embodiments, the cancer in the subject can include one or more of: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, stomach cancer, thyroid cancer, head and neck carcinoma, large bowel cancer, hematopoietic cancer, testicular cancer, colon and/or rectal cancer, uterine cancer, or prostatic cancer. In some embodiments, the cancer in the subject can be a metastatic cancer, including any one of bladder cancer, breast cancer, colon cancer, kidney cancer, lung cancer, melanoma, ovarian cancer, pancreatic cancer, prostatic cancer, rectal cancer, stomach cancer, thyroid cancer, or uterine cancer. In particular embodiments, the cancer is pancreatic cancer. In particular embodiments, the cancer is prostate cancer. In particular embodiments, the cancer is lung cancer.

In various embodiments, based on the cancer prediction, a therapeutic intervention can be selected for treating the cancer of the subject. The selected therapeutic intervention is likely to delay or prevent the development of the cancer. Exemplary therapeutic agents include chemotherapies, radiation, antigen-specific monoclonal antibodies, anti-inflammatories, oncolytic viral therapies, or immunotherapies. In various embodiments the therapeutic agent is a biologic, e.g. a cytokine, antibody, soluble cytokine receptor, antisense oligonucleotide, siRNA, etc. Such biologic agents encompass muteins and derivatives of the biological agent, which derivatives can include, for example, fusion proteins, PEGylated derivatives, cholesterol conjugated derivatives, and the like as known in the art. Also included are antagonists of cytokines and cytokine receptors. e.g. traps and monoclonal antagonists. Also included are biosimilar or bioequivalent drugs to the active agents set forth herein.

In various embodiments, the cancer prediction is a prediction for lung cancer. In such embodiments, based on the cancer prediction, a therapeutic intervention can be selected for treating the lung cancer. Example therapeutic interventions for lung cancer can include chemotherapeutics such as docetaxel, cisplatin, carboplatin, gemcitabine. Nab-paclitaxel, paclitaxel, pemetrexed, gefitinib, erlotinib, brigatinib (Alunbrig®), capmatinib (Tabrecta®), selpercatinib (Retevmo®), entrectinib (Rozlytrek®), lorlatinib (Lorbrena®), larotrectinib (Vitrakvi®), dacomitinib (Vizimpro®), and vinorelbine. Therapeutic agents for lung cancer can include antibody therapies such as durvalumab (Imfinzi®)), nivolumab (Opdivo®), pembrolizumab (Keytruda®), atezolizumab (Tecentriq®), canakinumab, and ramucirumab.

In various embodiments, the cancer prediction is a prediction for prostate cancer. In such embodiments, based on the cancer prediction, a therapeutic intervention can be selected for treating the prostate cancer. Therapeutic agents for prostate cancer can include a Poly (ADP-ribose) polymerase (PARP) inhibitor, Abiraterone Acetate. Apalutamide, Bicalutamide, Cabazitaxel, CASODEX (Bicalutamide), Darolutamide, Degarelix, Docetaxel, ELIGARD (Leuprolide Acetate), Enzalutamide, ERLEADA (Apalutanide) FIRMAGON (Degarelix), Flutamide, Goserelin Acetate, JEVTANA (Cabazitaxel), Leuprolide Acetate. LUPRON DEPOT (Leuprolide Acetate) LYNPARZA (Olaparib), Mitoxantrone Hydrocholoride, NILANDRON (Nilutamide), Nilutamide, NUBEQA (Darolutamide), Olaparib, ORGOVYX (Relugolix), PROVENGE (Sipuleucel-T), Radium 223 Dichloride, Relugolix, RUBRACA (Rucaparib Camsylate), Rucaparib Camsylate. Sipuleucel-T, TAXOTERE (Docetaxel), XOFIGO (Radium 223 Dichloride), XTANDI (Enzalutamide), YONSA (Abiraterone Acetate), ZOLADEX (Goserelin Acetate), and ZYTIGA (Abiraterone Acetate). In particular embodiments, a therapeutic agent for prostate cancer is a PARP inhibitor and specifically, ZEJULA (Niraparib).

In various embodiments, one or more of the therapeutic agents described can be combined as a combination therapy for treating the subject.

In various embodiments, a pharmaceutical composition can be selected and/or administered to the subject based on the cancer prediction for the subject, the selected therapeutic agent likely to exhibit efficacy against the cancer. A pharmaceutical composition administered to an individual includes an active agent such as the therapeutic agent described above. The active ingredient is present in a therapeutically effective amount, i.e., an amount sufficient when administered to treat a disease or medical condition mediated thereby. The compositions can also include various other agents to enhance delivery and efficacy, e.g. to enhance delivery and stability of the active ingredients. Thus, for example, the compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline. PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

The pharmaceutical compositions or therapeutic agents described herein can be administered in a variety of different ways. Examples include administering a composition containing a pharmaceutically acceptable carrier via oral, intranasal, intramodular, intralesional, rectal, topical, intraperitoneal, intravenous, intramuscular, subcutaneous, subdermal, transdermal, intrathecal, endobronchial, transthoracic, or intracranial method.

EXAMPLES

Figure 5:
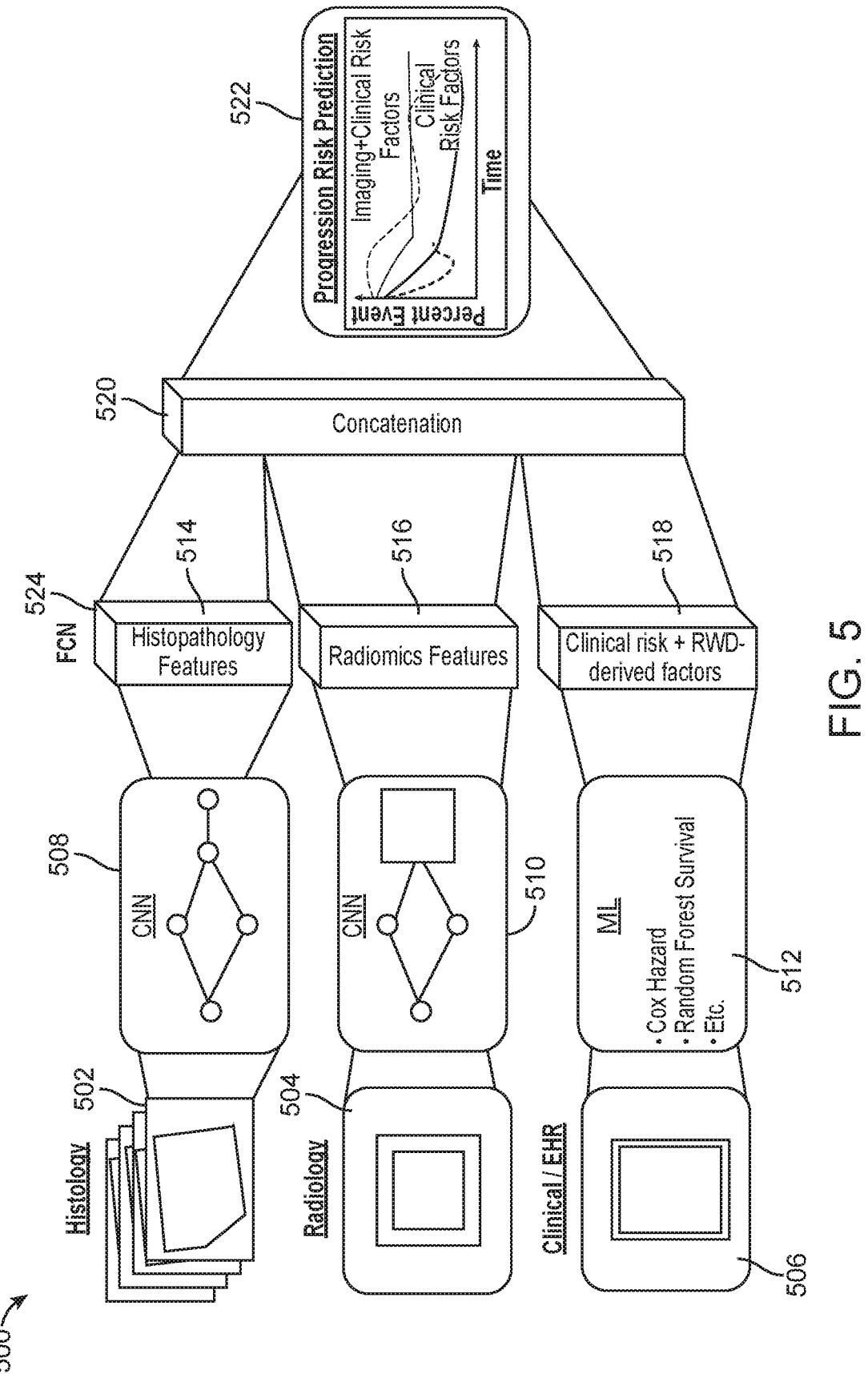
FIG. 5 illustrates a first example of a multimodal framework.

FIG. 5 depicts a first example of a multimodal framework 500. The multimodal framework 500 included multiple models (e.g., convolutional neural networks (CNN) 508, 510, and machine learning models (MLM)) 512 to integrate two distinct types of imaging data (e.g., histology images 502 and radiology images 504) and EHR 506 to provide histopathology features 514, radiomics features 516, and clinical risk and real-world data (RWD)-518 derived factors for concatenation 520 to provide as input into a FCN 524 to generate cancer predictions 522 (e.g., progression risk prediction or prognosis prediction in pan-cancer). The generated cancer predictions 522 were improved in comparison to classical assessments. The generated cancer predictions 522 from the multimodal framework could be used by: 1) clinicians or providers for clinical decision support; and 2) pharmaceutical companies to enrich for high-risk population for cancer trials.

Figure 6A:
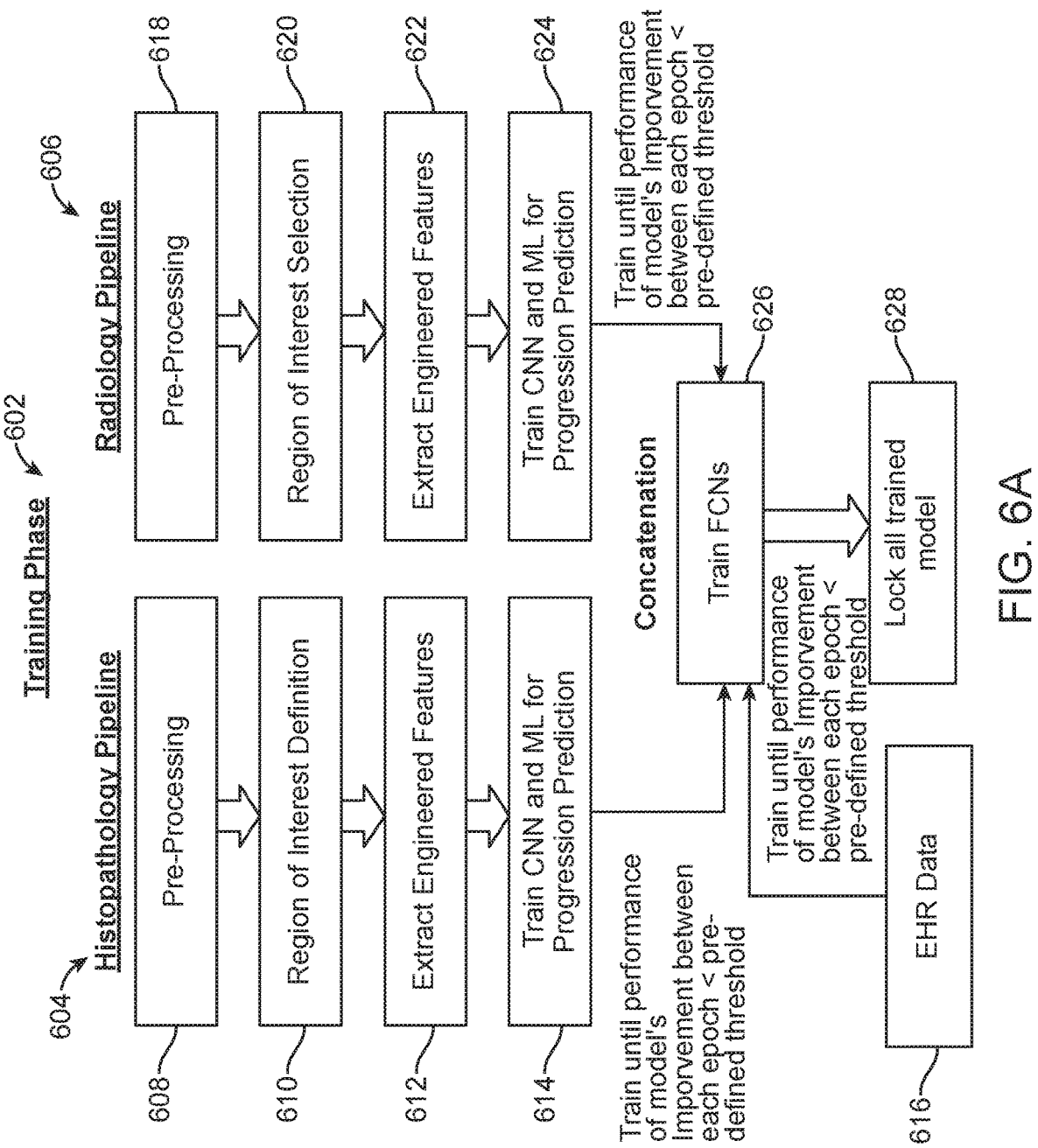
FIG. 6A illustrates an example training phase of a multimodal framework.
Figure 6B:
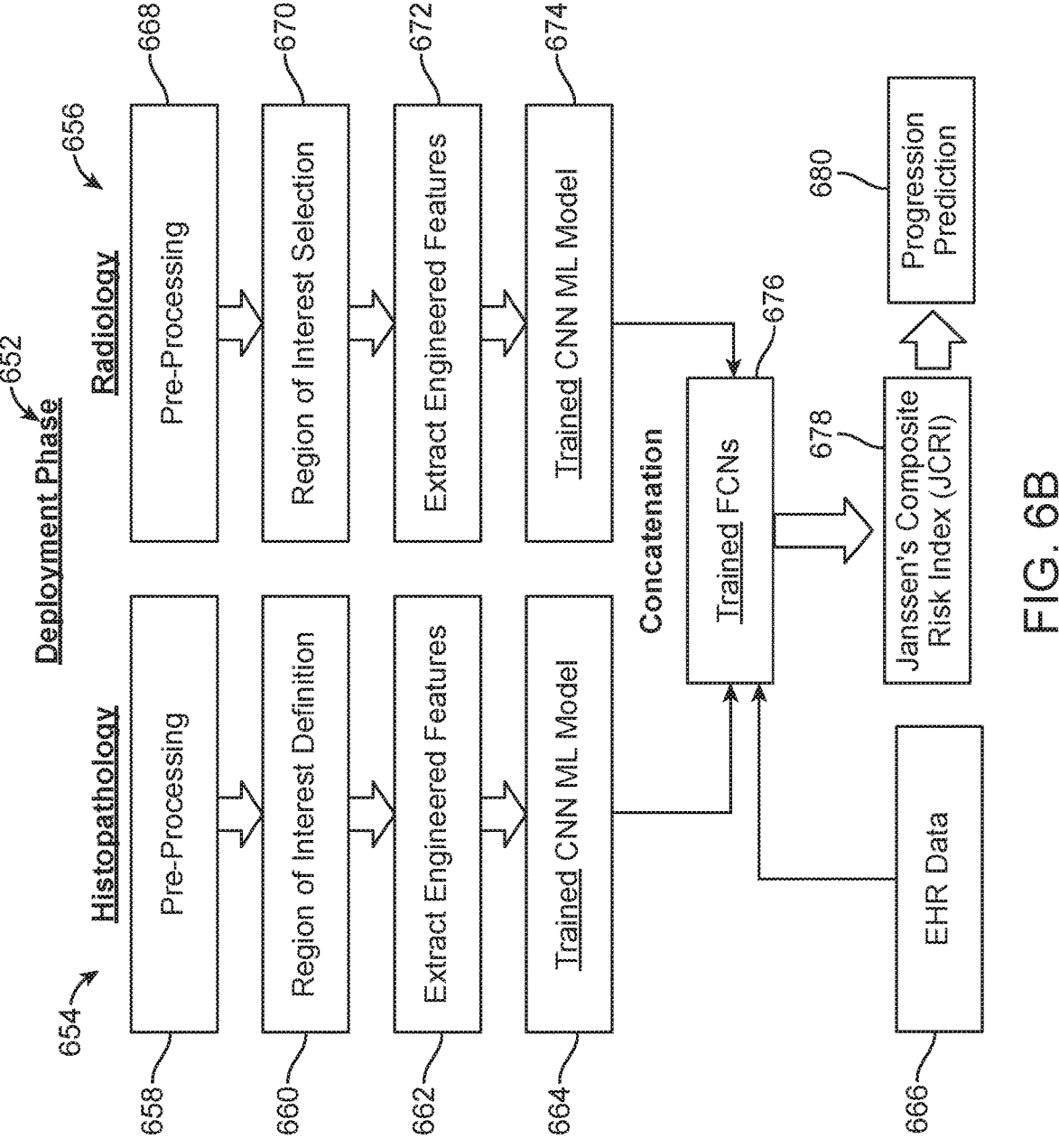
FIG. 6B illustrates an example deployment phase of a multimodal framework.

FIGS. 6A-B depict an example training phase 602 including a histopathology pipeline 604 and a radiology pipeline 606, and an example deployment phase 652 of a multimodal framework including a histopathology pipeline 654 and a radiology pipeline 656.

Referring to FIG. 6A, the training phase 602 included the following steps: (1) independently pre-processing histopathology 608 and radiology 618 images (e.g., "imaging data"); (2) independently segmenting the histopathology 610 and radiology 620 images for region of interest (ROI)

(e.g., tumor region): (3) independently extracting engineered features (e.g., textural features, cell counts) of the histopathology 612 and radiology 622 images; (4) feeding the images and corresponding extracted features (e.g., interpretable features) into CNN(s) and MLM(s) for training independently, wherein a set of CNN and a MLM was used for histopathology data 614, and another set of CNN and MLM was used for radiology data 624: (5) concatenating EHR data 616 and the outputs of CNNs and MLs for both histopathology and radiology data, and providing the concatenation into a fully connected network (FCN) for further training 626; and (6) halting trainings and locking all the trained CNN. ML models, and FCN 628.

Referring to FIG. 6B, the deployment phase 652 included the following steps: (1) independently pre-processing histopathology 658 and radiology 668 data (e.g., images); (2) independently segmenting the histopathology 660 and radiology 670 images for region of interest (ROI) (e.g., tumor region); (3) independently extracting engineered features (e.g., textural features, cell counts) of the histopathology 662 and radiology 672 images; (4) feeding the images and corresponding extracted features (e.g., interpretable features) into trained CNN(s) and MLM(s) for deployment, wherein a set of trained CNN and a MLM was used for histopathology data 664, and another set of trained CNN and MLM was used for radiology data 674; (5) concatenating EHR data 666 and the outputs of CNNs and MLs for both histopathology and radiology data into a trained fully connected network (FCN) for further deployment 676: (6) generating the output (e.g., Composite Risk Index (CRI)) from the trained FCN 678; and (7) using the generated CRI to predict risk of progression 680.

Figure 7:
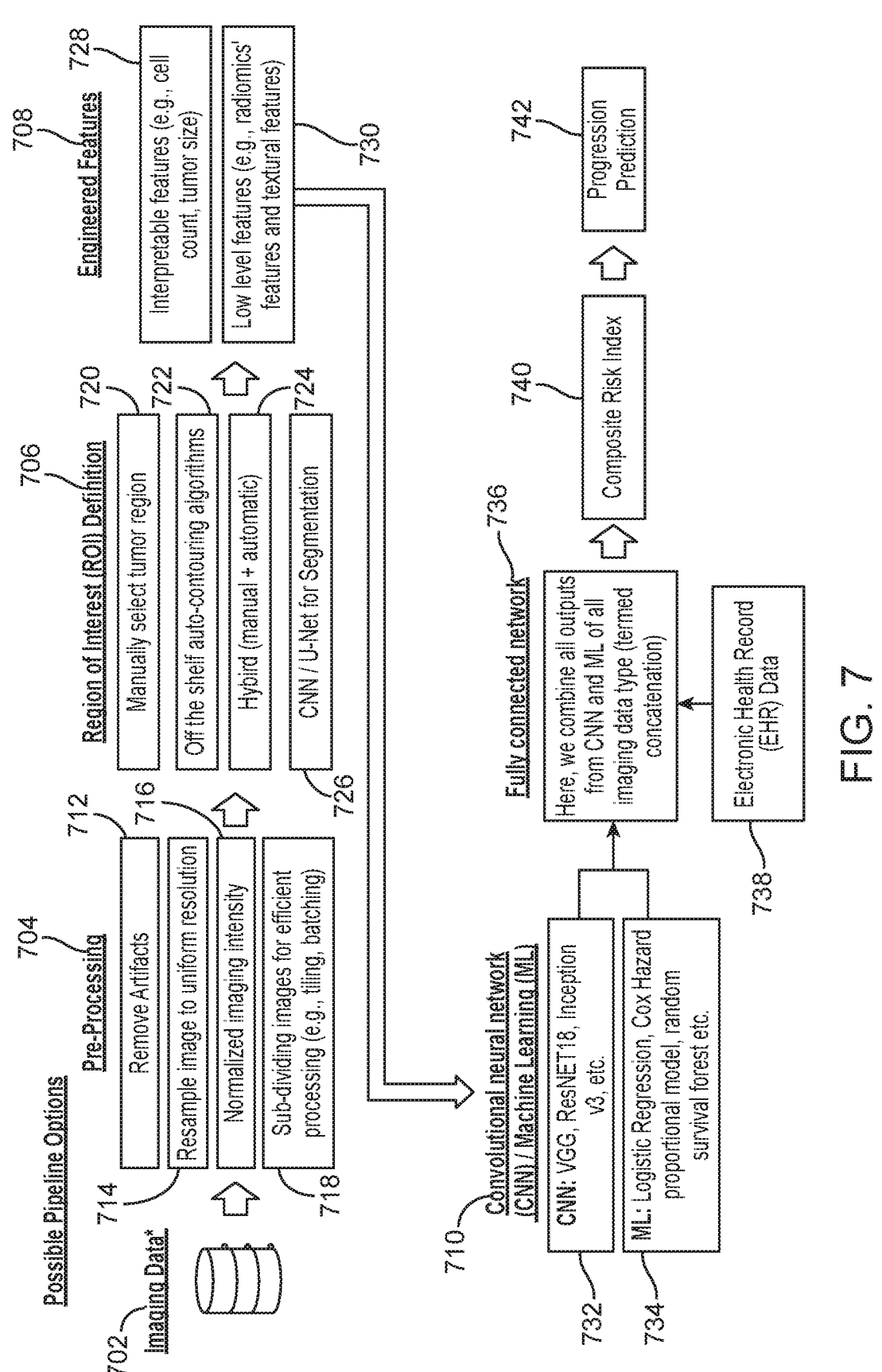
FIG. 7 illustrates a first example deployment pipeline of a multimodal framework.

FIG. 7 depicts a first example deployment pipeline of a multimodal framework. The pipeline included steps of pre-processing 704, region of interest (ROI) definition 706, feature engineering 708, model deployment 710 based on "Imaging Data" 702 including histopathology or radiology data to generate a cancer progression prediction. The pipeline was flexible and extensible as described herein. The step of pre-processing 704 included removing artifacts 712, resampling images to uniform resolution 714, normalizing imaging intensity 716, sub-dividing images for efficient processing (e.g., tiling, batching, etc.) 718, and other suitable pre-processing options. The step of region of interest (ROI) definition 706 included selecting tumor regions using any one of manually selection 720, "off the shelf auto-contouring algorithms." 722 combinations thereof 724, or other suitable options. In some scenarios, a CNN or U-Net 726 was used for segmentation of images. The step of feature engineering 708 included generating engineered features of the images that had been processed in the steps of pre-processing and ROI definition. The generated features were interpretable features 728 or low-level features 730, such as cell count, tumor size, interpretable radiomic features (e.g., tumor volume), interpretable textural features, and other interpretable features, as well as non-interpretable features such as definable radiomic features (e.g., gray-level co-occurrence matrices (GLCM)-entropy). The step of model deployment 710 did not depend on a particular CNN or ML model. For example, the CNN model could be any one of VGG, ResNet18, Inception v3, or other suitable models 732. As another example, the MLM could be any one of Logistic Regression, Cox Proportional-Hazards model, random survival forest or other suitable models 734. Furthermore, the output from the CNN and MLM, and EHR data 738 were provided to a FCN 736 to generate a composite risk index 740 that was informative of a cancer progression prediction 742 for a patient. As shown in FIG. 7, the multimodal framework enabled integration of different imaging types and EHR data. Thus, the multimodal framework was extensible to include additional imaging types or EHR data.

Figure 8:
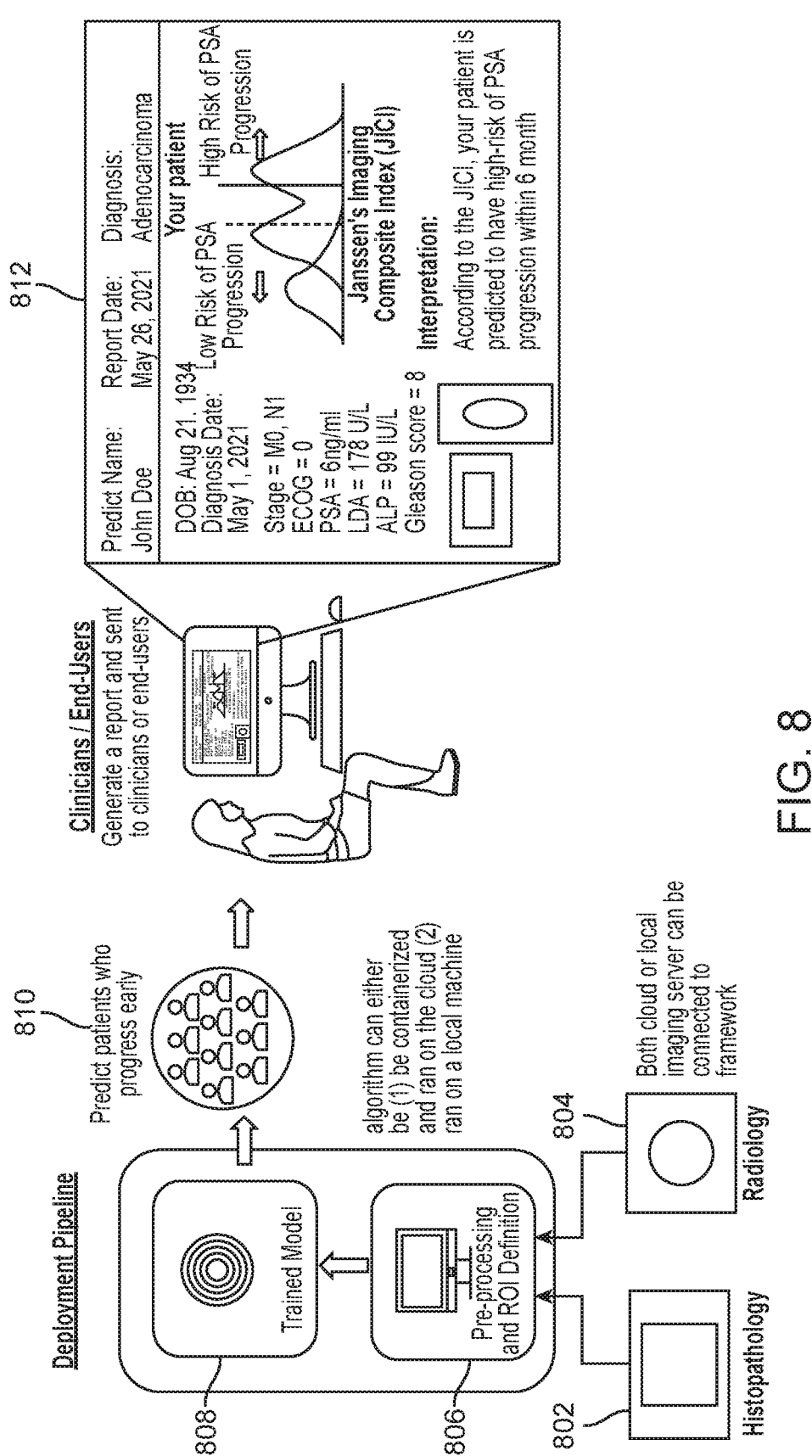
FIG. 8 illustrates a second example deployment pipeline of a multimodal framework

FIG. 8 depicts a second example deployment pipeline of a multimodal framework. The histopathology and radiology data were provided to the pipeline by connecting a cloud or a local imaging server to the multimodal framework. The histopathology 802 and radiology 804 images were processed using pre-processing 806 and ROI definition 808. In some scenarios, the pre-processing 806 and/or ROI definition 808 were based on an algorithm that was containerized and ran on the cloud, or an algorithm that was run on a local machine. The processed data were provided to trained models to generate output values (e.g., imaging composite index) informative of cancer prediction such as a risk of cancer progression in a patient 810. A report 812 of the cancer prediction for a patient generated from the models were sent to clinicians or end users for further use. The report included information such as a cancer that diagnosed (e.g., Adenocarcinoma), Diagnosis Date, Stage, ECOG, PSA, LDA, ALP, Gleason score, as well as a cancer prediction (e.g., a predicted risk level of cancer progression within a period of time for a patient).

Figure 10:
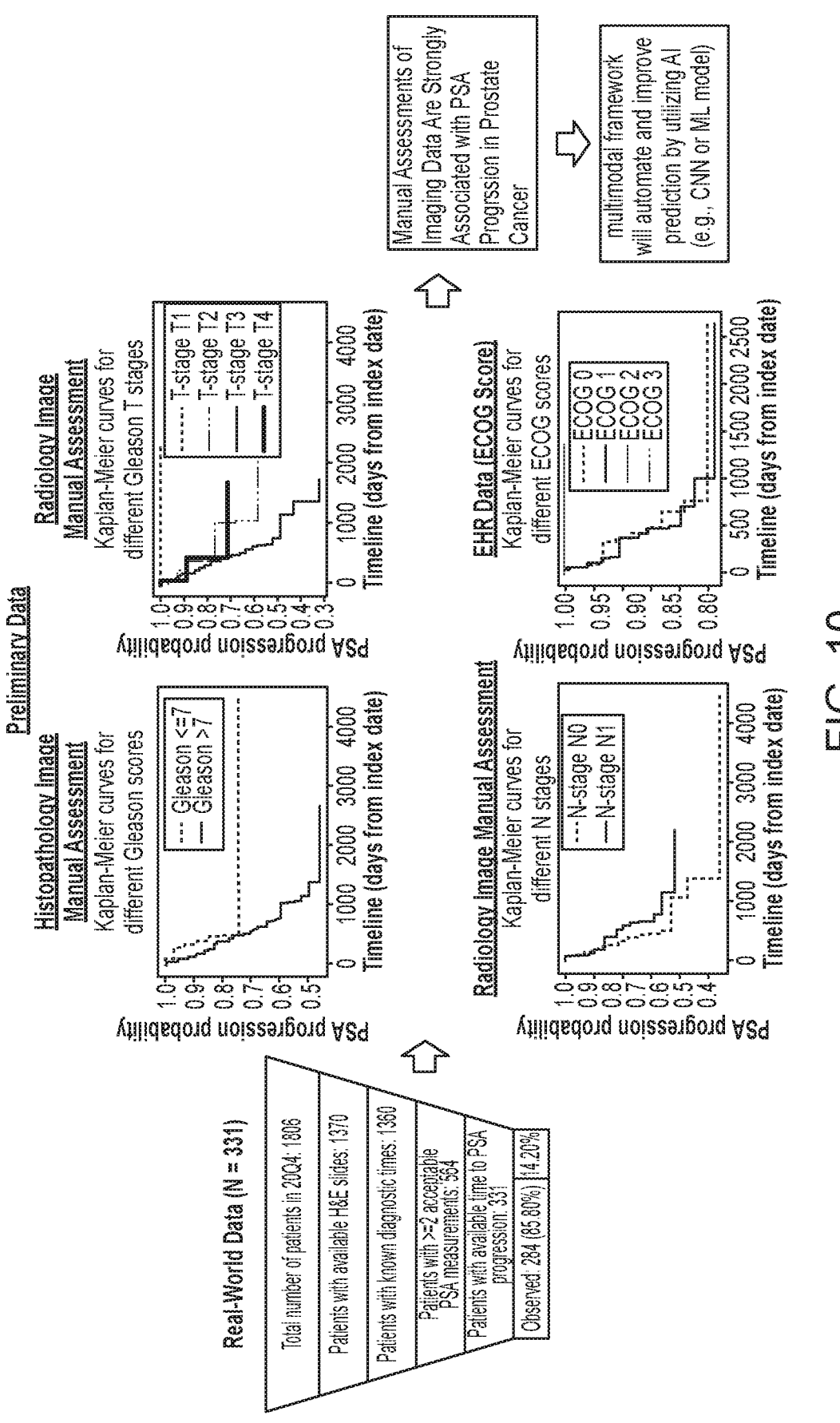
FIG. 10 illustrates an example of manual assessment of microscopic images, macroscopic images and EHR data in prostate cancer.

FIGS. 9 and 10 depict an example training phase of a multimodal framework based on histopathology data in prostate cancer. The example training phase as shown in FIGS. 9 and 10 includes both identification and validation of model parameters as described herein. In the study as shown in FIG. 9, 1806 patients were involved, among whom 1370 patients had available H&E slides (e.g., images). In the 1370 patients with available H&E slides, there were 1360 patients with known diagnostic times, wherein 564 of them had two or more acceptable prostate-specific antigen (PSA) measurements. In the 564 patients with two or more acceptable PSA measurements, there were 331 patients with available time to PSA progression. Finally, 284 (which is ~85.80%) of the 331 patients were observed and involved in the training of models in a multimodal framework. The training data including histopathology data of 198 patients (~64.71% of total) were split into training and validation sets. The histopathology data from 108 other patients (~35.29%) were used as a hold out test set. In some scenarios, the CNN or FCN could be provided by PNAS or other resources. In some scenarios, the models were trained and validated on independent randomized controlled trial (RCT) data that were stored independently in "SPARTAN" and "TITAN." The output of the CNN and EHR data were concatenated and provided as input to a FCN to generate patient PSA progression prediction. The multimodal framework could automatic and improve predictions using the CNN or ML models.

FIG. 10 depicts preliminary data showing that manual assessments of imaging data (e.g., histopathology and radiology image data) were strongly associated with cancer progression (e.g., PSA progression in prostate cancer). Notably, in the top row, both histopathology features and radiology features were used to, based on manual assessment, distinguish patients according to their survival time, as shown in the Kaplan Meier curves. Furthermore, in the bottom row, both radiology features and EHR data were used to distinguish patients according to their survival time, as shown in the Kaplan Meier curves.

Figure 12:
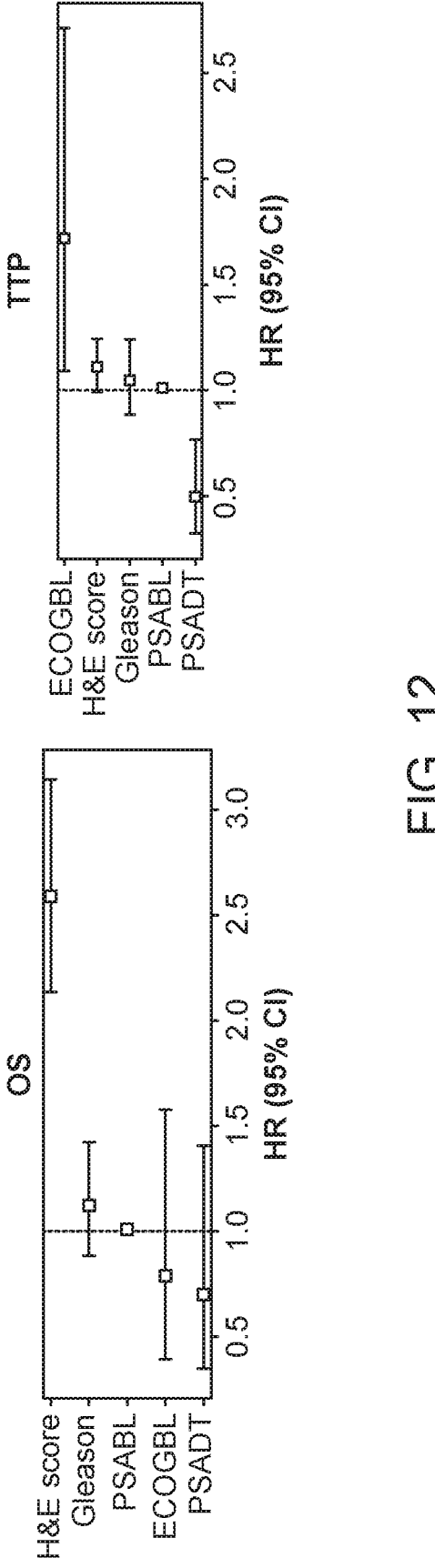
FIG. 12 is a set of plots for hazard ratios associated with example data relating to the described multimodal framework.

FIGS. 11-13 illustrates data associated with another example implementation of the cancer prediction system 130 as applied to predicting outcome in a cohort of patients with prostate cancer. In this example, the cohort included 154 non-metastatic castration-resistant (nmCRPC) patients in an ADT-treated placebo arm (PBO+ADT) of SPARTAN (NCT01946204) with available clinical data and H&E images (from archival Formalin-Fixed Paraffin-Embedded (FFPE) tumor collection). The patients were randomly divided into 70% (n=107) discovery and 30% (n=47) hold-out set. Randomization time was considered as the index date for time to event outcomes in SPARTAN trial. Overall Survival (OS) and Time to PSA Progression (TTP) were used as outcomes. Median TTP for PBO+ADT was approximately 3.7 months and follow-up time for OS was up to approximately 43 months.

In discovery, the multimodal approach described above included survival convolutional neural networks (SCNNs) as the trained CNNs 220 and a Cox proportional-hazards model (CPH) as the trained MLMs 230, each trained to learn time to event outcomes from the integration of imaging data and clinical features. The clinical model include baseline Age, BMI. Gleason score. ECOG (ECOGBL), PSA (PS-ABL), PSA doubling time (PSADT), T-Stage, N-Stage, baseline Testosterone, baseline Alkaline Phosphatase, baseline Hemoglobin levels. In this specific implementation. H&E Images were fed into the SCNN and the negative log likelihood of CPH were backpropagated to learn to output H&E risk scores associated with patient time to event. Clinical features are ingested into a CPH that learns to output clinical risk score and H&E and Clinical risk scores are integrated into another CPH that learns to output the multimodal risk score.

The above-described was trained on the discovery set to learn image and clinical representations that are associated with OS and TTP. After training and optimization on the discovery set the model was locked and its performance was evaluated on the holdout set. The model performance was quantified by concordance index (c-index). Kaplan-Meier (KM) analysis was used to evaluate the risk stratification. The thresholds to define risk categories in KM analysis were selected based on the risk values obtained in discovery set. The p-value of the log-rank test was used as the criteria for defining the cutoff point based on discovery set.

A multivariable Cox regression analysis was used to evaluate independent prognostic power of the H&E risk score and commonly used prognostic clinical features, including PSA, PSA doubling time, Gleason score, and ECOG score. This analysis was used to identify the main drivers in the multimodal approach. Forest plots were used to compare the ability of each feature in separating patients with poorer outcomes.

The performance of the multimodal approach had a concordance index (c-index) of 0.72 for OS and 0.73 for TTP, while clinical score only had a c-index of 0.62 for OS, and 0.64 for TTP. FIG. 11 illustrates example KM plots evaluating the multimodal risk stratification on holdout set for OS and TTP. The KM analysis illustrates significant separation of multimodal risk categories on hold-out set in both OS (p<0.005) and TTP (p=0.007). Risk categories (low, high) were generated by thresholding multimodal risks in discovery set. Based on the selected threshold 41% and 37% of holdout patients were categorized as high risk for OS and TTP, respectively.

Multivariable cox regression analysis indicates H&E risk has the more significant prognostic power for OS, and PSADT, PSABL and ECOGBL are the main drivers for TTP as shown in FIG. 12 and FIG. 13. FIG. 12 illustrates Forest plots for hazard ratios obtained through the multivariable cox regression analysis. As shown in FIGS. 12-13, multivariable cox regression analysis indicates H&E risk has the more significant prognostic power for OS, and PSADT. PSABL and ECOGBL are the main drivers for TTP. The above example thus demonstrates that the AI-based multi-modal risk score from clinical and H&E data is associated with outcomes in nmCRPC.

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

All references, issued patents and patent applications cited within the body of the instant specification are hereby incorporated by reference in their entirety, for all purposes.

The invention claimed is:

1. A method for developing a set of machine learning models for generating a cancer prediction for one or more prospective patients, comprising:

obtaining a batch of images captured from one or more patients, wherein obtaining the batch of images comprises obtaining a batch of microscopic training images comprising tissue structures and obtaining a batch of macroscopic training images comprising radiomic features;

training a first convolutional neural network model by providing, as input, the batch of microscopic training images until an improvement in first output data between each epoch of training is less than a first pre-defined threshold;

training a second convolutional neural network model by providing, as input, the batch of macroscopic training images until an improvement in second output data between each epoch of training is less than a second pre-defined threshold;

training a first machine learning model by providing, as input, extracted features from the batch of microscopic training images until an improvement in third output data between each epoch of training is less than a third pre-defined threshold;

training a second machine learning model by providing, as input, extracted features from the batch of macroscopic training images until an improvement in fourth output data between each epoch of training is less than a fourth pre-defined threshold;

locking the first and second convolutional neural network models and the first and second machine learning models;

generating a first set of output features from each epoch of training in the first convolutional neural network model and the first machine learning model;

generating a second set of output features from each epoch of training in the second convolutional neural network model and the second machine learning model;

obtaining a batch of electronic health record (EHR) data; and training a fully connected network by using the first set of output features, the second set of output features, and the batch of EHR data until an improvement in fifth output data between each epoch of training is less than a fifth pre-defined threshold.

2. The method of claim 1, wherein training the fully connected network using the first set of output features, the second set of output features, and the batch of EHR data comprises:

concatenating the first set of output features, the second set of output features, and the batch of EHR data into a feature vector; and training the fully connected network on the feature vector.

3. The method of claim 1, wherein training the first machine learning model comprises:

extracting first image features from the microscopic training images; and training the first machine learning model on the first image features, and wherein training the second machine learning model comprises:

extracting second image features from the macroscopic training images; and training the second machine learning model on the second image features.

4. The method of claim 1, wherein training the first convolutional neural network model comprises:

extracting first image features from the microscopic training images; and training the first convolutional neural network model on the first image features, and wherein training the second convolutional neural network model comprises:

extracting second image features from the macroscopic training images; and training the second convolutional neural network model on the second image features.

5. The method of claim 1, wherein the first convolutional neural network model and the second convolutional neural network model each comprises any one of a VGGNet model, a ResNet model, and an inception model.

6. The method of claim 1, wherein the first machine learning model and the second machine learning model each comprise any one of a logistic regression model, a cox proportional-hazards model, and a random survival forest model.

7. The method of claim 1, wherein the macroscopic training images comprise radiology images, and wherein the radiology images capture at least one of: one or more tumor areas, surrounding areas in proximity to the one or more tumor areas, or lymph nodes.

8. The method of claim 1, wherein the microscopic training images comprise histology images, and wherein the histology images capture at least one of: one or more cancer cells, lymphocytes, stromal cells, or epithelial cells.

9. The method of claim 1, wherein the fully connected network comprises any one of a neural network, a random forest, or a support vector machine.

10. The method of claim 1, wherein the fully connected network is trained to generate outputs informative of at least one of: the cancer prediction as a composite risk index, one or more treatment decisions, or clinical trial recruitment predictions.

11. A non-transitory computer-readable storage medium storing instruction for developing a set of models for generating a cancer prediction for one or more prospective patients, the instructions when executed by a processor causing the processor to perform steps comprising:

obtaining a batch of images captured from one or more patients, wherein obtaining the batch of images comprises obtaining a batch of microscopic training images comprising tissue structures and obtaining a batch of macroscopic training images comprising radiomic features;

training a first convolutional neural network model by providing, as input, the batch of microscopic training images until an improvement in first output data between each epoch of training is less than a first pre-defined threshold;

training a second convolutional neural network model by providing, as input, the batch of macroscopic training images until an improvement in second output data between each epoch of training is less than a second pre-defined threshold;

training a first machine learning model by providing, as input, extracted features from the batch of microscopic training images until an improvement in third output data between each epoch of training is less than a third pre-defined threshold;

training a second machine learning model by providing, as input, extracted features from the batch of macroscopic training images until an improvement in fourth output data between each epoch of training is less than a fourth pre-defined threshold;

locking the first and second convolutional neural network models and the first and second machine learning models;

generating a first set of output features from each epoch of training in the first convolutional neural network model and the first machine learning model;

generating a second set of output features from each epoch of training in the second convolutional neural network model and the second machine learning model;

obtaining a batch of electronic health record (EHR) data; and training a fully connected network by using the first set of output features, the second set of output features, and the batch of EHR data until an improvement in fifth output data between each epoch of training is less than a fifth pre-defined threshold.

12. The non-transitory computer-readable storage medium of claim 11, wherein training the fully connected network using the first set of output features, the second set of output features, and the batch of EHR data comprises:

concatenating the first set of output features, the second set of output features, and the batch of EHR data into a feature vector; and training the fully connected network on the feature vector.

13. The non-transitory computer-readable storage medium of claim 11, wherein training the first machine learning model comprises:

extracting first image features from the microscopic training images; and training the first machine learning model on the first image features, and wherein training the second machine learning model comprises:

extracting second image features from the macroscopic training images; and training the second machine learning model on the second image features.

14. The non-transitory computer-readable storage medium of claim 11, wherein training the first convolutional neural network model comprises:

extracting first image features from the microscopic training images; and training the first convolutional neural network model on the first image features, and wherein training the second convolutional neural network model comprises:

extracting second image features from the macroscopic training images; and training the second convolutional neural network model on the second image features.

15. The non-transitory computer-readable storage medium of claim 11, wherein the first convolutional neural network model and the second convolutional neural network model each comprises any one of a VGGNet model, a ResNet model, and an inception model.

16. The non-transitory computer-readable storage medium of claim 11, wherein the first machine learning model and the second machine learning model each comprise any one of a logistic regression model, a cox proportional-hazards model, and a random survival forest model.

17. The non-transitory computer-readable storage medium of claim 11, wherein the microscopic training images comprise histology images, and wherein the histology images capture at least one of: one or more cancer cells, lymphocytes, stromal cells, or epithelial cells.

18. The non-transitory computer-readable storage medium of claim 11, wherein the macroscopic training images comprise radiology images, and wherein the radiology images capture at least one of: one or more tumor areas, surrounding areas in proximity to the one or more tumor areas, or lymph nodes.

19. The non-transitory computer-readable storage medium of claim 11, wherein the fully connected network comprises any one of a neural network, a random forest, or a support vector machine.

20. A computer system comprising:

a processor; and a non-transitory computer-readable storage medium storing instruction for developing a set of models for generating a cancer prediction for one or more prospective patients, the instructions when executed by the processor causing the processor to perform steps comprising:

obtaining a batch of images captured from one or more patients, wherein obtaining the batch of images comprises obtaining a batch of microscopic training images comprising tissue structures and obtaining a batch of macroscopic training images comprising radiomic features;

training a first convolutional neural network model by providing, as input, the batch of microscopic training images until an improvement in first output data between each epoch of training is less than a first pre-defined threshold;

training a second convolutional neural network model by providing, as input, the batch of macroscopic training images until an improvement in second output data between each epoch of training is less than a second pre-defined threshold;

training a first machine learning model by providing, as input, extracted features from the batch of microscopic training images until an improvement in third output data between each epoch of training is less than a third pre-defined threshold;

training a second machine learning model by providing, as input, extracted features from the batch of macroscopic training images until an improvement in fourth output data between each epoch of training is less than a fourth pre-defined threshold;

locking the first and second convolutional neural network models and the first and second machine learning models;

generating a first set of output features from each epoch of training in the first convolutional neural network model and the first machine learning model;

generating a second set of output features from each epoch of training in the second convolutional neural network model and the second machine learning model;

obtaining a batch of electronic health record (EHR) data; and training a fully connected network by using the first set of output features, the second set of output features, and the batch of EHR data until an improvement in fifth output data between each epoch of training is less than a fifth pre-defined threshold.

* * * * *